US012214140B2

(12) United States Patent
Fox

(10) Patent No.: US 12,214,140 B2
(45) Date of Patent: Feb. 4, 2025

(54) ADAPTIVE DIGITAL THERAPY SYSTEM WITH REAL-TIME EMOTIONAL STATE ANALYSIS AND SYMBOLIC LANGUAGE COMMUNICATION

(71) Applicant: Brian Patrick Fox, Chicago, IL (US)

(72) Inventor: Brian Patrick Fox, Chicago, IL (US)

( * ) Notice: Subject to any disclaimer, the term of this patent is extended or adjusted under 35 U.S.C. 154(b) by 0 days.

(21) Appl. No.: 18/670,815

(22) Filed: May 22, 2024

(65) Prior Publication Data

US 2024/0416067 A1    Dec. 19, 2024

Related U.S. Application Data

(60) Provisional application No. 63/521,665, filed on Jun. 17, 2023.

(51) Int. Cl.
*A61M 21/00*        (2006.01)

(52) U.S. Cl.
CPC ..... *A61M 21/00* (2013.01); *A61M 2021/0022* (2013.01); *A61M 2021/0027* (2013.01);
(Continued)

(58) Field of Classification Search
CPC .......... A61M 21/00; A61M 2021/0022; A61M 2021/0027; A61M 2021/005; A61M 2021/0077; A61M 2230/10
See application file for complete search history.

(56) References Cited

U.S. PATENT DOCUMENTS

| 11,810,337 | B2 | 11/2023 | Wu et al. | |
| 2003/0033145 | A1* | 2/2003 | Petrushin | G10L 17/26 704/236 |

(Continued)

OTHER PUBLICATIONS

Benchetrit, Banville, and King. Toward a real-time decoding of images from brain activity. Meta Blog Post Published Oct. 18, 2023.
(Continued)

*Primary Examiner* — Carrie R Dorna
*Assistant Examiner* — Joshua Daryl D Lannu
(74) *Attorney, Agent, or Firm* — Colorado Venture Patents LLC

(57) ABSTRACT

The present invention relates to a system and method for providing adaptive digital therapy, enhancing the emotional well-being of users through the analysis and translation of expressive and physiological states. Aspects of the invention are directed to identifying the neuroplastic window via user inputs, with or without the aid of psychedelics. This invention is particularly suited for supporting psychoactive therapies involving compounds such as 5-HT2A agonists, dissociatives, and empathogens, as well as applications beyond psychoactive treatments. By utilizing multi-modal deep learning methods, the system captures a wide array of user inputs, including text, speech, vision, symbols, and brain waves, to form a dynamic user representation. This representation is then used to provide real-time, tailored generative communications informed by established psychological therapeutic frameworks. The invention features a closed-loop feedback system through an access module, enabling continuous data relay, patient response metric derivation, and transmission of emotional optimization communications. The system also introduces novel communication methods, including symbolic language input, to articulate complex experiences and extends its capabilities to include natural emotional states, broadening its therapeutic applicability.

18 Claims, 9 Drawing Sheets

(52) U.S. Cl.
CPC .............. *A61M 2021/005* (2013.01); *A61M 2021/0077* (2013.01); *A61M 2230/10* (2013.01)

(56) References Cited

U.S. PATENT DOCUMENTS

| | | | |
|---|---|---|---|
| 2010/0046842 A1* | 2/2010 | Conwell | G06F 18/24 382/218 |
| 2020/0104641 A1* | 4/2020 | Alvelda, VII | G06N 3/045 |
| 2021/0169389 A1* | 6/2021 | Moskowitz | A61B 5/28 |

OTHER PUBLICATIONS

Gold, Joshua and Ciorciari, Joseph, A Review on the Role of the Neuroscience of Flow States in the Modern World. Behav Sci (Basel). Sep. 2020; 10(9): 137.

R L Carhart-Harris, K J Friston. Rebus and the Anarchic Brain: Toward a Unified Model of the Brain Action of Psychedelics. Pharmacol Rev. Jul. 2019;71(3):316-344. doi: 10.1124/pr.118.017160.

* cited by examiner

SEEKER

⇧ Home
⊙ Guide
↕ Self
⚎ Clients

Hello brian@seeker-flow.io

Patient: Brian

Primary Diagnosis

Search ICD-10 Codes... ▽

[ Insights ] [ Chat ] [ Metrics ] [ Notes ]

Enter notes about your session...

Save Notes

Log Out

SEEKER

⌂ Home
◎ Guide
♦ Self
♣ Clients

Hello brian@seeker-flow.io

Patient: Brian

[ Insights ] [ Chat ] [ Metrics ] [ Notes ]

You:
Hello ! Could you give me a brief outline of the patient?

Seeker:
Certainly. Brian Fox is experiencing a sense of disturbance from a lingering issue he describes metophorically as a "ghost reminiscence" or a "lingering bug," suggesting unresolved emotions or thoughts from the past. Brian expresses cautious optimism about overcoming the issue, yet uncertainty remains. He seemse to be on a journey towards self-integration, facing the complexities of personal growth. The conversation suggests a focus on internal reactions to this persistence, and Brian seeks to transform these remnants into elements of a cohesive narrative of resilience and perserverance.

| What have been the prevailing stratagies of Brian's Managers in response to this recurring issue? | How have Brian;s Firefighters reacted historically to the reemergence of this "ghost" and what impact has this had on his system? | In what ways might Brian's Exiles be influencing his current expereince of the "lingering bug" or "ghost reminiscence"? |

Ask anything...                          [Send]  🎤

Log Out

*FIG.7*

ADAPTIVE DIGITAL THERAPY SYSTEM WITH REAL-TIME EMOTIONAL STATE ANALYSIS AND SYMBOLIC LANGUAGE COMMUNICATION

CROSS-REFERENCE TO RELATED APPLICATIONS

This application claims the benefit of U.S. Provisional Patent Application 63/521,665 filed on Jun. 17, 2023, which is incorporated by reference in its entirety.

TECHNICAL FIELD OF THE INVENTION

The technical field of the invention encompasses data processing and artificial intelligence methods for creating a two-way communication system that facilitates adaptive digital therapy and other uses, including the use of psychoactive compounds, by monitoring and interpreting physiological activity and enhancing emotional well-being through the analysis and translation of expressive and physiological states.

BACKGROUND OF THE INVENTION

The field of mental health treatment has seen a growing interest in the incorporation of biometric data capture to enhance therapeutic outcomes. Prior art in this domain has focused on developing technologies to monitor physiological signals, such as heart rate, brain activity, and other biometric indicators. These technologies aim to provide a quantitative basis for understanding a patient's emotional and psychological state, particularly in the context of therapies involving psychoactive compounds.

During psychological states characterizable as flow states, individuals experience transient hypofrontality, a phenomenon where there is a temporary reduction in the activity of the prefrontal cortex. This reduction helps minimize distractions and self-referential thoughts, allowing a person to become fully immersed in the task at hand. This state not only enhances the brain's performance and efficiency by allowing other regions to operate more effectively but also promotes neuroplasticity. The focused and sustained attention required during flow states strengthens neural connections related to the skills being utilized, leading to improved performance and the acquisition of new abilities. Furthermore, transient hypofrontality supports neuroplasticity by reallocating resources to brain regions directly involved in the ongoing task. This efficient redistribution of cognitive load facilitates the reinforcement of neural pathways and promotes long-term changes in brain structure and function. Despite these benefits, there remains a significant need for systems that can effectively integrate and leverage these concepts to enhance mental health therapies.

Moreover, the interplay between transient hypofrontality, flow states, and neuroplasticity provides significant insights into learning, mental health, and rehabilitation. It is well understood in the relevant art that engaging in activities that induce flow states not only enhances neuroplasticity but also facilitates the acquisition and improvement of skills. This is because the focused attention and reduced prefrontal cortex activity characteristic of flow states make it easier to learn new skills and refine existing ones. Additionally, flow states are linked to increased happiness and well-being, suggesting that activities promoting flow can have beneficial effects on mental health by reducing stress and enhancing overall life satisfaction. In the context of rehabilitation and therapy, techniques that leverage transient hypofrontality and flow can significantly aid in the recovery of cognitive and motor functions by boosting neuroplasticity, thereby enabling more effective and rapid rehabilitation outcomes. Given these benefits, there is a clear need for systems that can harness these phenomena to support and enhance learning, mental health therapies, and rehabilitation processes.

Some psychedelic therapies traditionally involve the use of psychoactive substances, such as LSD, psilocybin, MDMA, and ayahuasca, which are known to induce profound changes in perception, mood, and cognitive processes. Such changes are sometimes associated with boosting neuroplasticity. Medically accepted uses of these substances are emerging, particularly in controlled clinical trials and research settings, where they are being investigated for their potential to treat a range of mental health disorders, including treatment-resistant depression, post-traumatic stress disorder (PTSD), and end-of-life anxiety. However, outside of these medical contexts, the use of psychedelics often falls into non-therapeutic and frequently illegal realms, with individuals using these substances for recreational purposes or personal exploration, which can lead to legal repercussions and health risks due to the lack of professional oversight. Despite the challenges, the deployment of psychedelic therapies holds significant opportunities, especially if advancements can be made in safely integrating these compounds into therapeutic protocols, monitoring their effects with precision, and scaling their application to benefit a larger segment of the population in need of innovative mental health interventions.

In order to create such therapeutic protocols, the capture of evaluable information such as biometric data is necessary. However, capturing biometric data during the use of psychedelics presents unique challenges. The altered states of consciousness induced by these substances can lead to significant fluctuations in biometric readings, which complicates the task of obtaining consistent, reliable and actionable data. Prior art has struggled to account for the high variability and potential artifacts in the data collected during such experiences. Moreover, the subjective nature of psychedelic experiences makes it difficult for users to provide accurate self-reports, which are often used to complement biometric data.

The prior art also includes efforts to process and analyze the collected biometric data to identify trends and generate actionable insights. These efforts involve the use of algorithms and statistical models to interpret the data and correlate it with emotional and cognitive states. However, the individual variability in response to psychoactive compounds poses a significant challenge to these models. The prior art has not fully addressed the need for personalized and adaptive systems that can learn from each user's 2090 unique biometric patterns and provide tailored insights.

Despite advancements in biometric data capture and analysis, there remains a need for systems that can integrate this data with therapeutic protocols effectively. Prior art has not yet provided a solution that bridges the gap between the subjective experiences of users under the influence of psychedelics and the objective assessments of clinicians. There is a need for a platform that can offer real-time feedback and support to users, ensuring that they remain in suitable emotional states throughout their therapeutic journey.

While prior art has laid the groundwork for the use of biometric data in mental health therapies, there remains a significant need for improved methods and systems. These systems must be capable of handling the complexities of biometric data capture during psychedelic use, identifying individualized trends and insights, and integrating these findings into effective therapeutic protocols. The fulfillment of these unmet needs would represent a substantial advancement in the field of mental health treatment and support the wellbeing of individuals and populations on a broader scale, particularly as psychedelics continue to enter the realm of generally acceptable supervised medical therapies.

Still, the persistent utilization of psychedelics outside of supervised medical contexts introduces many risks and challenges. Without the guidance of medical professionals, individuals may encounter difficulties in dosage regulation, setting, and managing the psychological aftermath of their experiences. The absence of structured therapeutic support can lead to potential adverse effects, such as ontological shock or destabilization, particularly for first-time users or those with underlying mental health conditions. Moreover, the unsupervised use of these substances can result in legal and safety concerns, as well as the potential for misuse or abuse. The lack of a controlled environment and professional oversight means that the therapeutic potential of psychedelics may be compromised, and the risks of harm may be elevated. Yet often the tools and knowledge appropriately associated with clinical environments and that pertain to the use of psychedelics remain unavailable.

More particularly, on an individual level, the lack of evaluation of psychedelic therapies presents a significant barrier to understanding their efficacy and optimizing treatment protocols. Each individual's psychological makeup and response to psychoactive compounds are unique, making it imperative to assess the impact of such therapies on a case-by-case basis. Without personalized monitoring and analysis, it is challenging to tailor treatments to individual needs, potentially leading to suboptimal outcomes or unaddressed adverse reactions. Likewise, on a population level, the absence of comprehensive data collection and analysis associated with psychedelics hinders the ability to draw broader conclusions about the effectiveness of these therapies across diverse demographics. This gap in evaluation also limits the advancement of evidence-based practices and the development of standardized protocols that could enhance the safety and efficacy of psychedelic therapies for the wider public.

Sentiment analysis, a technique commonly used in the field of data processing and artificial intelligence, involves the computational understanding and classification of affective states expressed through text, speech, or other forms of communication. In the context of psychedelic therapy, sentiment analysis could play a crucial role in interpreting and quantifying the subjective experiences of individuals undergoing treatment. Dimethyltryptamine (DMT), a powerful psychedelic compound naturally occurring in some plants and animals, is known for inducing intense and brief hallucinogenic experiences. It has been the subject of research for its potential therapeutic effects, particularly in the treatment of various mental health conditions. Despite its promise, the use of DMT in therapeutic settings has not been widely adopted, as the rapid onset and profound nature of the experiences it induces can be challenging to navigate and interpret, particularly without supporting tools.

Within the context of psychedelic therapy, a significant problem arises from the absence of a robust informatics framework that can effectively utilize semantics to interpret the profound and often ineffable experiences induced by these substances. Traditional semantic analysis tools are not designed to capture the non-linear, non-dual, and deeply subjective nature of psychedelic experiences, which can involve complex visual and emotional phenomena that defy conventional language. This gap in informatics means that the nuanced understanding of these altered states is largely uncharted, leaving therapists and researchers without the means to systematically analyze and integrate the rich data that psychedelic experiences can offer. Consequently, the potential for informatics to enhance the therapeutic process, improve outcomes, and contribute to the scientific understanding of consciousness and healing remains largely untapped in the field of psychedelic therapy.

While the therapeutic potential of psychedelics is increasingly recognized, significant challenges persist in their application outside of supervised medical contexts and absent the individualized evaluation of their effects. The risks associated with unsupervised use, coupled with the absence of tailored therapeutic assessment, underscore the pressing need for innovative solutions. These solutions should aim to provide structured support, ensure safety, and optimize treatment efficacy on both individual and population levels. As the landscape of mental health treatment evolves, it is clear that there are unmet needs in the integration of psychedelics into mainstream therapeutic practices, highlighting an opportunity for advancements that could transform the field and improve patient outcomes.

SUMMARY OF THE INVENTION

Aspects of the present invention include a comprehensive system for analyzing and enhancing a user's 2090 emotional well-being through adaptive digital therapy. This system is designed to support both psychoactive therapies involving compounds such as 5-HT2A agonists, dissociatives, and empathogens, as well as non-psychoactive treatments. By leveraging multi-modal deep learning methods, exemplary implementations of the invention capture and processing a wide range of user inputs 2020, including text, speech, vision, symbols, and brain waves, to form a dynamic user representation. This real-time classification of the user's 2090 emotional state is then utilized to provide tailored generative communications, such as audio, video, and text, which are informed by established psychological therapeutic frameworks. The preferred embodiment of the invention includes a closed-loop feedback system that operates through an access module, enabling continuous data relay, patient response metric derivation, and transmission of emotional optimization communications, thereby facilitating ongoing monitoring and support for the user's 2090 therapeutic journey.

Addressing the need for scalable technologies to enhance the safety and efficacy of psychoactive compounds, the preferred embodiment of the present invention provides a novel method for users to digitally self-report their dynamic emotional states, inclusive of labeled compounds. The method encompasses transmitting user data through an access module, transcribing and processing inputs to determine emotional expression and valence, and mapping these to therapeutic frameworks for real-time adaptation. The system's ability to transmit generative communications back to the user and modify them based on metric responses allows for a personalized and responsive therapeutic experience. This approach addresses the current limitations in therapist availability and the high costs associated with traditional therapy models, offering a scalable solution for emotional well-being support.

Embodiments of the invention introduce symbolic language input aspects that enable users to communicate complex experiences during extended state sessions, such as those involving subconscious renderings or interactions with various intelligences. This method is particularly advantageous for articulating experiences that are challenging to express with conventional language, as often encountered in psychedelic therapy sessions. Additionally, the invention's capability extends to deriving user representations based on natural emotional states, without the influence of ingested compounds. This broadens the system's applicability to a wider range of therapeutic contexts, making it a versatile tool for enhancing mental health treatment and supporting well-being on a broader scale.

BRIEF DESCRIPTION OF THE FIGURES

FIG. 4 depicts a session progress user interface in association with an exemplary embodiment.

Figure 5:
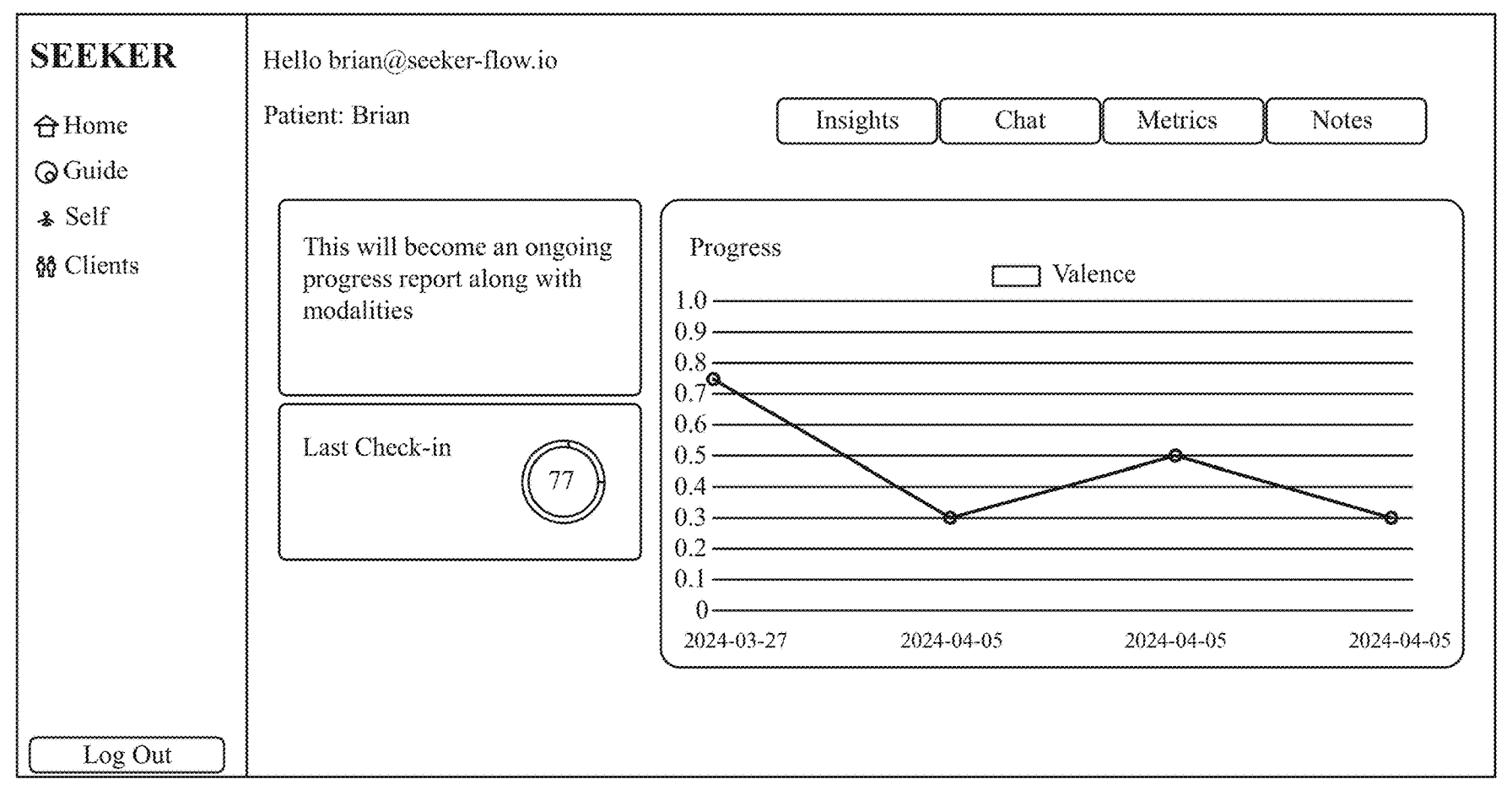

FIG. 5 depicts a subject user's progress graph user interface in accordance with an exemplary embodiment.

FIG. 7 depicts communications module user interface in accordance with an exemplary embodiment.

DETAILED DESCRIPTION

Figure 1:
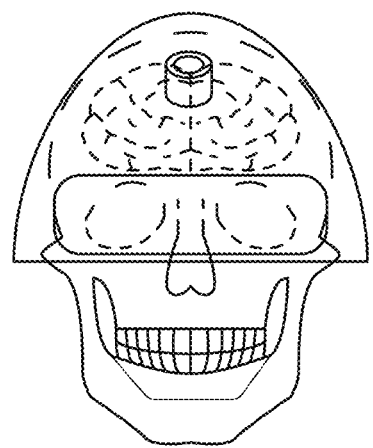
FIG. 1 depicts aspects of the system comprising a holographic lens and the external projection of a representation of the user's brain in accordance with a treatment environment in association with an exemplary embodiment.
Figure 2A:
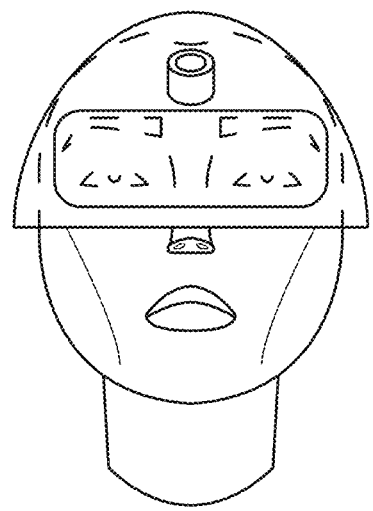
FIG. 2A depicts aspects of the system comprising a holographic lens and the utilization of such aspects in accordance with an intended use in an exemplary embodiment.
Figure 2B:
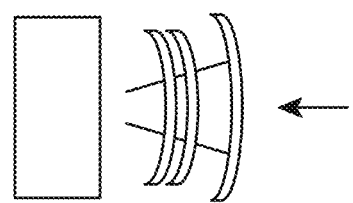
FIG. 2B depicts the direction of a holographic projection upon aspects of a lens in accordance with aspects of an exemplary embodiment.

Aspects of the present invention comprise a system for the analyzation of a user's 2090 expressive and physiological state to inform patient self-management and clinical care, and enhancing the therapeutic treatment of patients, including the monitoring of psychoactive therapies (e.g., 5-HT2A agonists (e.g., LSD and psilocybin), dissociatives, and empathogens) through self-reporting interfaces (e.g., mobile and wearable devices, EEG, fMRI machines and human neural interfaces). The client's inputs 2020, streaming and static, are logged via multi-modal deep learning methods; text, speech, vision, symbols, and brain waves, and mapped to quantized expressive and psychological data points, forming a dynamic user representation. The resulting real-time classification of the user's 2090 emotional state is provided to the user 2090 and their clinical support system (e.g., psychiatrists, psychologists and physicians). The user representation is compared to established psychological therapeutic frameworks to transmit generative communications (e.g., audio, video, text, symbols, optogenetic neural modulation) to elevate the client's emotional state and guide a process of intelligent adaptation. In particular, the preferred embodiment provides a closed loop, real-time, feedback system via an access module capable of relaying data, deriving patient response metrics and transmitting emotional optimization communications, while enabling clinicians to monitor emotional trends and provide necessary psychological assessment, and support, prior to, during, and in lieu of therapeutic appointments.

A psychedelic journey is understood as an alteration of consciousness, often characterized by the dissolution of the ego and the experience of mystical states that can lead to significant psychological healing. Participants in such journeys frequently report transcending conventional perceptions of time and space, gaining transformative insights into the fundamental nature of reality, and experiencing a deep sense of unity with the universe, concepts that resonate with the psychological theories of Carl Jung and the mythological frameworks of Joseph Campbell. The visual and sensory experiences range from detailed scientific visualizations to deeply symbolic and spiritual imagery. This enhanced perception is believed to result from the ability of psychoactive therapies to relax the brain's normal restrictive functions, expanding perceptual boundaries and facilitating the reconfiguration of neural pathways, which is crucial for trauma recovery. In some circumstances, similar visual and sensory experiences can result without the assistance of psychedelic substances. These experiences often exceed the capacity of humans to provide ordinary articulation to describe or communicate them. They also often leave enduring impacts on individuals' perspectives and life philosophies.

In the context of the present invention, the concept of the "journey" is integral as it leverages these transformative experiences to enhance therapeutic outcomes. The system comprising an embodiment of the invention captures and analyzes the rich data generated during these psychedelic journeys, utilizing advanced algorithms to map and sustain the beneficial states encountered. By systematically enhancing understanding of each user's 2090 journey and integrating these profound experiences into structured therapeutic frameworks, the preferred embodiment facilitates not just acute healing but also long-term psychological growth and well-being, making the ephemeral benefits of a psychedelic journey accessible and beneficial in everyday life.

Visualization of Archetypal Journey Contents:

Aspects of the preferred embodiment enable the visualization of a user's 2090 internal experiences during a therapeutic session, often referred to as the "in-journey" phase. This is achieved by projecting images derived from the user's 2090 brain activity, allowing clinicians and users to visually observe the archetypal contents of the journey. In association with an embodiment, the functional alignment between AI systems and the brain guides the generation of images that resemble what participants perceive. While the reconstructed images may not perfectly replicate the original stimuli, they preserve high-level features such as object categories, demonstrating the potential of magnetoencephalography (MEG), in capturing complex brain representations in an example.

Neural Interface and Projection Technology:

In association with such embodiment, the system utilizes neural interfaces, including MEG, EEG, or fMRI, to capture the brain's electrical patterns linked to various cognitive and emotional states experienced during the journey. Advanced algorithms process these patterns and convert them into visual representations. The visual content generated can be displayed in real-time using projection technology, effectively creating a visual map of the user's 2090 journey. Additionally, this visual content can be streamed directly to a display, such as a TV, and saved as a video file. For an immersive viewing experience, the stream can also be stereoscopically streamed for use with a Virtual Reality (VR) headset. Furthermore, the content can be recorded and rendered within a game engine, allowing for subsequent playback and detailed study within a VR environment.

In the preferred embodiment, the system incorporates a neuro-visual interface that integrates neural monitoring devices, such as MEG, EEG, and/or fMRI, with projection systems. This interface is designed to capture the brain's electrical activity and analyze it using machine learning algorithms that are specifically trained to recognize patterns associated with distinct visual archetypes or symbolic imagery. The processed data is then converted into visual content, which is projected onto a screen or other appropriate surfaces within the therapeutic environment. For example, during a session involving psilocybin, a user 2090 might vividly experience archetypal imagery, such as encountering a 'wise old man' or 'great mother' figure. The neuro-visual interface identifies the neural signatures linked to these profound experiences and transforms them into visual representations, which could range from abstract patterns to more defined figures, depending on the clarity of the neural data and the sophistication of the algorithms. These images are projected in real-time, enabling both the user 2090 and clinician to observe and interact with the visual manifestations of the user's 2090 inner experiences. The system facilitates a dynamic visual feedback loop, where the projected content is continuously adjusted in real-time based on changes in the user's 2090 neural activity, reflecting shifts in emotional or cognitive states. This interactive visual experience closely mirrors the user's 2090 internal journey, adding a significant layer of engagement and potential therapeutic intervention.

Post-session, the user 2090 and clinician can review the journey, enhancing the therapeutic process by discussing the visualized experiences. During the session, the clinician monitors the imagery while the system logs the archetypal imagery, aiming to identify and catalog universal symbolic language patterns. These patterns are recorded in a library, which serves as a resource to decode and translate this symbolic language, facilitating a deeper understanding of the universal themes that emerge during psychedelic experiences. This approach not only aids in interpreting the user's 2090 journey but also ensures the protection of the content against misuse, maintaining the integrity of the therapeutic process and safeguarding against potential nefarious alterations of the visual content. The ultimate goal is to map the user's 2090 journey accurately, translate the universal language observed, and ensure ethical use of this powerful therapeutic tool.

Embodiments utilize MEG, a non-invasive neuroimaging technique, to capture the brain's activity with high temporal resolution. Such embodiments incorporate aspects to decode and visualize the unfolding of visual representations in the brain, contributing to the understanding of how sensory signals are transformed into meaningful representations. The present inventor acknowledges that while fMRI provides spatially precise neuroimaging, MEG offers the advantage of millisecond precision, enabling the real-time tracking of the brain's representational dynamics. In various embodiments the use of one or the other or both is preferred dependent upon the specific use case. The continuous flux of images decoded from MEG activity complements the spatial precision of fMRI, offering a more comprehensive understanding of brain function. Embodiments of the invention comprise an AI system capable of decoding brain activity into visual content. This system comprises three key components: an image encoder, a brain encoder, and an image decoder. The image encoder processes visual stimuli independently of the brain, creating a set of image representations. The brain encoder aligns the MEG, EEG and/or fMRI signals with these image embeddings, and the image decoder reconstructs the perceived images based on the aligned brain representations. In an embodiment, MEG, EEG and/or fMRI recordings are continuously aligned with deep representations of images, which condition the generation of visual content at each instant. This allows for a continuous stream of images decoded from brain activity, providing a dynamic visualization of the user's 2090 perceptual experience.

Deep Learning for Archetypal Content Interpretation:

The preferred embodiment employs deep learning models, including those as further described herein, trained on extensive datasets that correlate specific neural patterns with known archetypal imagery and symbols commonly reported in psychoactive therapy sessions. These models decode the MEG, EEG and/or fMRI data to identify and categorize the unique electrical patterns associated with the user's 2090 internal experiences. In an exemplary embodiment, the AI system is trained on public datasets of MEG, EEG and/or fMRI recordings from healthy volunteers, such as those released by the Things initiative. This training enables the system to align brain signals with state-of-the-art computer vision AI systems, like DINOv2, which learn visual representations in a self-supervised manner without human annotations.

Real-Time Feedback and Adjustment:

By visualizing the user's 2090 journey, the system provides real-time feedback to both the user 2090 and an associated clinician. This feedback can be used to adjust the therapeutic protocol dynamically, ensuring that the therapy is responsive to the user's 2090 immediate needs. For example, if the visualized content indicates an emerging negative experience, the system can prompt the clinician to intervene or can automatically generate soothing auditory or visual stimuli to guide the user 2090 back to a positive state. In an embodiment, the system delivers text created via generative artificial intelligence technologies to mediate negative experiences or reinforce enhanced states encountered during usage of the system.

Integration with Therapeutic Frameworks:

The visual representations of the user's 2090 journey are compared against established psychological therapeutic frameworks to ensure that the visual content is interpreted within a clinically relevant context. This integration allows clinicians to better understand the user's 2090 experiences and to provide more effective post-session integration support.

Aspects of the invention are directed to a comprehensive system that supports individuals throughout the entire therapeutic journey, encompassing pre-session, session, and post-session phases, with a focus on cultivating emotional homeostasis and monitoring the use of compounds.

Pre-Session Preparation:

Prior to the therapy session, the system in an embodiment engages in preparatory activities to establish a baseline of the user's 2090 emotional state. This is achieved through sentiment analysis of user inputs, such as mood logs, self-reported feelings, and physiological data collected via wearable devices. The system may also gather information on any compounds the user plans to utilize, ensuring that the upcoming session is tailored to the individual's current state and therapeutic needs. This pre-session data contributes to a personalized approach, setting the stage for a more effective therapeutic experience.

Session Monitoring:

During the therapy session itself, the system in an embodiment continues to monitor the user's 2090 emotional state through real-time sentiment analysis. This involves evaluating verbal and non-verbal cues, physiological responses, and other relevant inputs to provide a continuous assessment of the user's 2090 well-being. The system's ability to log and analyze the compounds used during the session allows for a nuanced understanding of the user's 2090 reactions and the effects of the therapy. In one exemplary embodiment, by avoiding direct involvement in the psychedelic journey or therapy sessions, the system maintains a supportive role, focusing on safety and emotional regulation. In various embodiments, direct involvement in sessions of aspects of the system is preferred, such as through altering images in the brain or delivering stimuli to the user 2090 via audio, light or text. In particular, direct involvement may provide benefit by mediating the experience for the user.

Post-Session Integration:

Following the therapy session, the system's role in an embodiment becomes crucial in facilitating integration and maintaining emotional balance. Generative communications, which may include personalized messages, therapeutic content, and guided exercises, are delivered to the user. In an exemplary embodiment, the generative communications delivered comprise a representation of a user's 2090 visual contents during the user's 2090 journey and/or therapy session. In accordance with various aspects of an embodiment, the generative communications are derived from a library of universal symbols from the collective activities of one user 2090 or a plurality of users. These communications are informed by the sentiment trends and compound logs recorded throughout the pre-session and session phases. The novel application of generative communications in the context of post-psychedelic therapy represents an innovative approach to supporting users as they assimilate their experiences into their daily lives. The system's ongoing trend analysis helps users achieve and maintain emotional homeostasis, contributing to long-term well-being. In an embodiment, following the session, the system analyzes the journal entries created in association with its use to identify the archetypal narrative. In an embodiment, the visual content captured during the journey can be reviewed and analyzed, offering valuable material for integration therapy. Clinicians can discuss the projected images with the user, helping to interpret and integrate the meanings and insights derived from the visualized archetypes into the user's 2090 personal growth and healing process.

Further in association with the preferred embodiment of the invention, the system is specifically tailored to enhance the therapeutic treatment of patients undergoing psychoactive therapies, including but not limited to the use of psychedelics such as 5-HT2A agonists (for example, LSD and psilocybin), dissociatives, and empathogens. These substances have shown promise in the treatment of various mental health conditions, and the system is designed to support and optimize their therapeutic potential. Aspects of an embodiment focus on analyzing the impact of psychoactive compounds on the user's 2090 emotional and cognitive states. By correlating specific compounds, dosages, and administration schedules with sentiment and physiological responses, the system can guide the selection and dosage of compounds for enhanced therapeutic outcomes.

The system achieves this by analyzing a user's 2090 expressive and physiological state through a comprehensive set of self-reporting interfaces, which may include mobile and wearable devices, EEG, fMRI machines, and human neural interfaces. These interfaces collect a wide range of data, from spoken words and facial expressions to brain waves and other physiological markers. This data is then processed using multi-modal deep learning methods to create a dynamic representation of the user's 2090 emotional and psychological state. Embodiments integrate a wider array of multimodal data, such as micro-expressions, HRV, tone inflections, and other physiological readings to achieve a more nuanced understanding of the user's 2090 emotional state. This data informs the system's real-time adjustments to the therapeutic content, enhancing the personalization of the therapy.

This real-time user representation is particularly relevant in the context of psychedelic therapy, where the patient's emotional and cognitive experiences can be profound and rapidly changing. By providing real-time classification of the user's 2090 emotional state, the system can offer immediate feedback to both the user 2090 and their clinical support team, which may include psychiatrists, psychologists, and physicians. This feedback is crucial for ensuring the safety and efficacy of the psychedelic experience, allowing for timely interventions if necessary. Exemplary embodiments of the invention incorporate user representations that utilize predictive analytics to anticipate future emotional states of the user. These embodiments employ machine learning algorithms to analyze historical data and identify patterns, enabling the system to proactively tailor therapeutic interventions to the user's 2090 needs.

The concept of homeostasis, a fundamental principle in developmental robotics, is integral to the system's approach to therapeutic intervention. In robotics, homeostasis refers to the system's ability to maintain internal stability and adapt to external changes to preserve its functionality. This principle is applied to both self-preservation behaviors and learning mechanisms. Similarly, an embodiment of the invention models user 2090 needs and drives, suggesting behaviors that help maintain these within a safe homeostatic range, thereby guiding users toward a state of equanimity.

The system employs algorithms to model the user's 2090 physiological and psychological needs, including via machine learning, akin to the way developmental robots might monitor their operational parameters. These models take into account various factors such as stress levels, emotional states, and cognitive load, which are analogous to a robot's energy levels, sensor integrity, and processing capacity. By continuously monitoring these factors, the system can detect when a user 2090 is approaching the limits of their homeostatic range.

Upon identifying a potential imbalance, the system proactively suggests behaviors or interventions that can restore homeostasis. For instance, if the user's 2090 stress levels are detected to be high, the system might recommend relaxation techniques, mindfulness exercises, or other stress-reducing activities. In an embodiment, such techniques comprise vibratory frequencies, audio, and/or pulsed light. These suggestions are personalized based on the user's 2090 historical data and current state, ensuring that the interventions are both relevant and effective. The ultimate goal of maintaining homeostasis is to guide the user 2090 toward equanimity—a balanced and stable emotional state. The system's interventions are designed to not only address immediate imbalances but also to promote long-term emotional regulation skills. By learning from each interaction with the user, the system refines its understanding of the user's 2090 needs and improves its ability to provide timely and appropriate support. By ensuring that the user's 2090 needs are met and their emotional state is stable, the system creates a conducive environment for learning and growth. This mirrors the way developmental robots use homeostatic mechanisms to protect themselves and facilitate the acquisition of new skills.

Furthermore, in an embodiment the system actively engages with all aspects of the therapeutic journey, including the actual session, to promote healing. It achieves this by comparing the user representation 3000 against established psychological therapeutic frameworks and utilizing generative communications, such as audio, video, text, and optogenetic neural modulation. In an embodiment, photobiomodulation is utilized, which typically refers to a form of therapy that uses non-ionizing light sources, including lasers, LEDs, and broadband light, in the visible and infrared spectrum to stimulate healing, reduce inflammation, and alleviate pain. These tools are designed to positively influence the user's 2090 emotional state throughout the entire process. This comprehensive approach is especially crucial during the psychedelic therapy session itself, where real-time adjustments in the generative communications can significantly aid in navigating the experience. Additionally, this strategy extends into the integration phase of psychedelic therapy, where the patient endeavors to assimilate their profound experiences into their everyday life. By addressing both the in-session and post-session phases, the system ensures a holistic therapeutic experience that supports the user 2090 in achieving lasting healing and integration. The closed-loop, real-time feedback system provided by the access module is a cornerstone of the preferred embodiment, enabling the relay of data and the derivation of patient response metrics. This system allows for the transmission of emotional optimization communications, which can be adjusted dynamically based on the patient's response. Clinicians are thus empowered to monitor emotional trends and provide necessary psychological assessment and support, not only during scheduled therapeutic appointments but also before and after the psychedelic sessions, which is critical for patient safety and the long-term success of the therapy.

Figure 9:
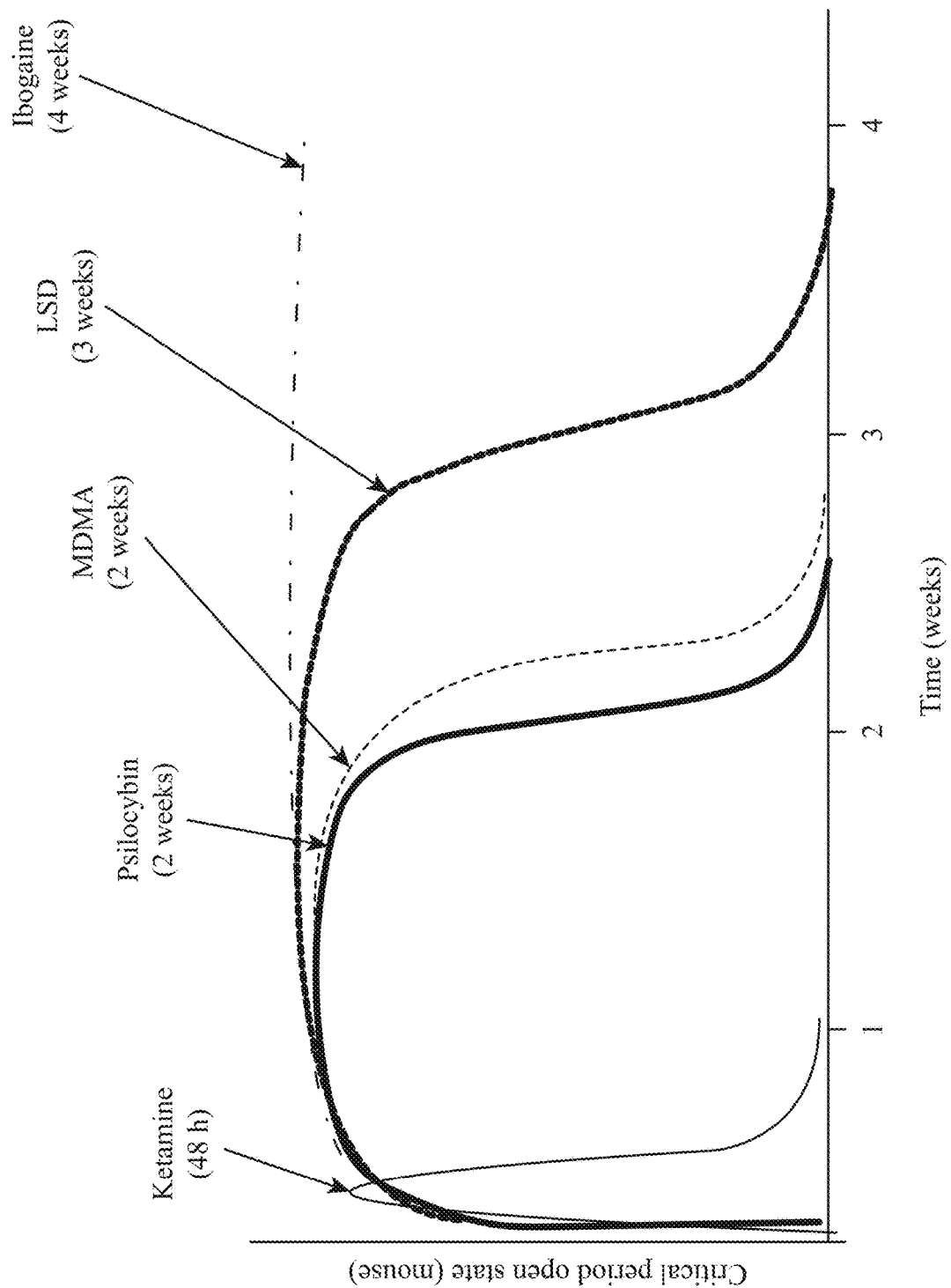
FIG. 9 depicts a graph presenting the timing of neuroplasticity windows in association with various psychedelic substances in accordance with an exemplary embodiment.

As depicted in FIG. 9, the use of a mouse model offers a foundational understanding of how labeled compounds influence neuroplastic windows. By labeling such compounds and tracking their effects, the system can establish a baseline for the onset of neuroplastic windows in humans. Once these labeled compounds are administered to human users, the access module plays a crucial role in capturing and transmitting user data during the neuroplastic windows identified post-journey. This data includes not only physiological responses but also semantic data, which is analyzed to understand the cognitive and emotional states experienced by the user 2090 during these windows. The integration of this information into the system's model allows for a comprehensive understanding of how specific compounds influence neuroplasticity and associated cognitive states. Furthermore, the system's ability to recognize and sustain these states in everyday life, even without the administration of psychedelics, is enhanced by the continuous analysis of user data during neuroplastic windows. This includes data from flow states, characterized by transient hypofrontality, and non-dual states as observed in long-term meditators through fMRI and semantic analysis. By mapping these states to the optimized states of the Hierarchical Multimodal Self-Organizing Map (HSOM), the system can effectively identify and replicate the conditions that promote such states, thereby facilitating sustained cognitive and emotional well-being. This capability offered by the access module in an embodiment includes transmitting initial user data inclusive of labeled compounds, and continuously capturing and analyzing subsequent data to refine and enhance the system's predictive and adaptive functionalities. This ongoing process ensures that the system remains responsive to the evolving research and user experiences, thereby improving its effectiveness in supporting neuroplasticity and overall mental health.

An aspect of the preferred embodiment comprises a feedback loop system designed to facilitate communication through direct brain interaction, enhanced by the use of psychedelic compounds. During an exemplary use, this system leverages the altered states of consciousness and heightened neural connectivity induced by psychedelics to enable a person to communicate in a room of light without relying on traditional verbal or written language.

This feedback loop allows for real-time adaptation and personalization of the communication process. As the system learns more about the individual's unique neural patterns and how they correlate with the light signals, it can refine its encoding and decoding algorithms to improve the accuracy and depth of the communication. This could enable individuals to express complex thoughts and emotions in a direct and intuitive manner, potentially opening up new avenues for therapeutic intervention and exploration of consciousness.

Aspects of the preferred embodiment facilitate the feedback loop through machine learning. An embodiment incorporates meta-learning models, which are machine learning (ML) frameworks designed to optimize the learning process of other ML models. These meta-learners play a crucial role in enhancing the system's ability to facilitate cyclical integration over multiple therapeutic journeys. By tuning the hyperparameters of subordinate ML models, meta-learning algorithms can significantly improve the efficiency and effectiveness of the learning mechanisms within the system.

Hyperparameters are the settings and configurations that govern the structure and behavior of ML models. Meta-learning models in the system are tasked with identifying the optimal hyperparameters that allow subordinate models to adapt quickly and accurately to the user's 2090 changing emotional and cognitive states. This optimization process is critical for personalizing therapy, as it ensures that the ML models can fine-tune their responses to the unique needs of each user, even as those needs evolve over time.

In the context of the preferred embodiment, the therapeutic journey is inherently cyclical, with users undergoing multiple cycles of experience, reflection, and integration. Meta-learning models support this process by enabling subordinate ML models to build upon the knowledge acquired in previous cycles. This longitudinal learning approach allows the system to develop a deeper understanding of the user's 2090 patterns and progress, leading to more nuanced and impactful therapeutic interventions in subsequent cycles.

Meta-learning models are particularly adept at handling the diverse range of experiences and data encountered during therapeutic journeys. They enable subordinate ML models to generalize from past experiences and quickly adapt to new ones, reducing the time and data required to reach effective therapeutic outcomes. This efficiency is crucial for supporting users through the integration process, where timely and relevant interventions can make a significant difference in the user's 2090 well-being.

The meta-learning framework also contributes to the continuous improvement of the system as a whole. By constantly evaluating the performance of subordinate ML models and adjusting their hyperparameters, the meta-learners ensure that the system is always operating at its best. Embodiments of the invention achieve this by perpetually monitoring the performance metrics of subordinate machine learning (ML) models and fine-tuning their hyperparameters to optimize functionality. In an embodiment, this ongoing optimization process means that the system becomes more effective over time, with each user's 2090 journey contributing to the collective intelligence of the therapeutic platform. This process of continuous evaluation and adjustment by the meta-learners is instrumental in maintaining the platform's operational excellence.

In an embodiment, the meta-learning framework is linked to the identification and utilization of neuroplasticity windows-critical periods when the brain's capacity for reorganization and the formation of new neural connections is at its peak. The timing of occurrence of such neuroplasticity windows in accordance various substances each contemplated for use in association with an embodiment is presented in FIG. 7. In an embodiment, the platform employs a weighted sentiment analysis algorithm that processes user input data to calculate unique scores. These scores are not arbitrary but are weighted according to the relevance and impact of the emotional expressions detected in the user's 2090 input, thereby providing a nuanced assessment of the user's 2090 emotional state. The calculated scores serve as indicators of the user's 2090 current neuroplastic potential. When these scores align with the characteristics of neuroplastic windows, the system recognizes this as an opportune moment for delivering targeted therapeutic interventions. By leveraging the calculated scores to pinpoint these windows, the system can introduce personalized therapeutic content that is specifically designed to harness the heightened neuroplasticity, thereby facilitating more profound and lasting cognitive and emotional development. Furthermore, the meta-learning framework incorporates these calculated scores into its optimization cycle. As the system interacts with users over multiple therapeutic journeys, it aggregates the score data to refine its understanding of individual and collective neuroplasticity patterns. This data-driven approach enables the system to progressively improve its predictive models, ensuring that each user's 2090 therapeutic journey is not only informed by their own experiences but also enriched by the collective insights gained from the wider user base.

In the realm of psychedelic therapy, the application of informatics through semantics holds particular relevance as it provides a structured approach to understanding and navigating the non-ordinary states of consciousness that these substances can induce. Psychedelics often lead to experiences that transcend typical dualistic frameworks of language, challenging individuals to articulate their experiences that are beyond the conventional verbal descriptors. By leveraging semantic informatics-analyzing and interpreting the complex, often symbolic language used by individuals during these non-dual states-therapists and researchers can gain deeper insights into the cognitive and emotional landscapes encountered. This understanding is crucial for guiding individuals through their experiences, integrating them into their broader psychological framework, and ultimately harnessing the therapeutic potential of psychedelics to facilitate profound personal growth and healing. Embodiments of the invention are specifically designed to direct individuals towards non-dual states using language alone. This is achieved through natural language processing algorithms that analyze and generate communications capable of guiding the user's 2090 consciousness into states typically associated with psychedelic experiences. The system's ability to induce such states without the use of substances represents a novel approach to therapy and personal growth. An embodiment incorporates the concept of implicit processes alongside the non-dual experiences typically associated with psychedelic therapy. In such way, an embodiment harnesses semantic informatics to delve into the subconscious undercurrents that drive our thoughts and behaviors. By engaging with the implicit processes—those automatic, often unconscious psychological mechanisms that influence perception and decision-making—the system can facilitate a deeper exploration of the psyche. This exploration is particularly potent in non-dual states, where the boundaries between the conscious and unconscious are more permeable, allowing for a more integrated and holistic experience of self. In an embodiment, natural language processing algorithms are thus designed not only to guide users into non-dual states through language but also to navigate the rich tapestry of implicit processes that underlie these transformative experiences, offering a comprehensive approach to personal development and self-actualization without the need for psychedelic substances.

In the context of embodiments of the invention, notably the integration of narrative therapy with Jungian, Gestalt, and Internal Family Systems approaches, such embodiments provide a sophisticated framework for personal development and self-actualization. The system employs a scoring mechanism that discerns the user's 2090 current phase within their personal narrative, akin to the stages of the Hero's Journey—a monomyth described by Joseph Campbell that outlines a common pattern of transformation found in global myths. For example, the Hero's Journey typically involves phases such as the Call to Adventure, Refusal of the Call, Meeting the Mentor, Crossing the Threshold, Trials and Tribulations, Approach to the Inmost Cave, the Ordeal, Reward (Seizing the Sword), The Road Back, Resurrection, and Return with the Elixir. By identifying the user's 2090 position within this archetypal journey, the system can deliver tailored content and therapeutic prompts that resonate with the specific challenges and opportunities characteristic of that phase. In an exemplary embodiment, in association with the 'Call to Adventure' stage, the system might present scenarios that encourage the user 2090 to confront their fears or hesitations, thereby facilitating the initial step towards transformation. In another exemplary embodiment, during an 'Abyss' or 'Death and Rebirth' phase, the system could provide reflective exercises that help the user 2090 navigate through their deepest struggles, promoting insight and fostering resilience. As the user 2090 progresses to a 'Return' phase, the system would shift to support the integration of new insights into the user's 2090 life, reinforcing the growth and changes they have undergone. The system's content delivery is dynamic, adapting not only to the user's 2090 narrative phase but also to their responses and evolving self-concept. It incorporates elements from Gestalt therapy to enhance present awareness and mindfulness, Jungian archetypes to tap into the collective unconscious, and Internal Family Systems to harmonize the various sub-personalities within the individual. This multifaceted approach ensures that the user 2090 is supported through every step of their journey, with the system acting as a digital guide that mirrors the support traditionally provided by a therapist in psychedelic-assisted therapy sessions. In such manner, an embodiment of the invention represents a digital therapeutic ally, harnessing the power of narrative and the depth of psychological archetypes to induce transformative states that parallel those experienced in psychedelic therapy.

Embodiments of the invention integrate the principles of narrative therapy with the insights of narrative neuroscience to foster a singular narrative of self-actualization for the individual, as a user 2090 of the platform. This holistic approach is predicated on the understanding that the stories individuals tell about their lives have a profound impact on their identity and psychological well-being. By aligning narrative therapy, which focuses on the re-authoring of personal narratives, with narrative neuroscience, which studies how the brain constructs narratives, the platform presents a unique framework for personal transformation. The system in embodiments comprises natural language processing (NLP) algorithms that not only analyze the content and emotional undertones of the user's 2090 communications but also actively participate in the narrative construction process. These algorithms are designed to recognize patterns, themes, and archetypes within the user's 2090 narrative, providing insights that can be used to reshape the user's 2090 narrative towards one of self-actualization and fulfillment. In practice, the platform facilitates the user's 2090 journey towards non-dual states of consciousness by employing language, audiovisual signals, frequency signals and/or light as a therapeutic tool. In accordance with the preferred embodiment, the NLP algorithms generate communications that resonate with the user's 2090 experiences and aspirations, effectively guiding their consciousness towards states of unity and interconnectedness that are often encountered during psychedelic experiences. This guidance is achieved by crafting narrative interventions that challenge dualistic thinking and encourage the user 2090 to perceive themselves and their experiences as part of a cohesive, integrated whole. In accordance with the preferred embodiment, the narrative interventions are personalized and adaptive, taking into account the user's 2090 ongoing narrative as well as their cognitive and emotional development. By doing so, the system supports the user 2090 in constructing a narrative that is not only coherent and meaningful but also aligned with their intrinsic values and goals, thereby promoting self-actualization. Thus, embodiments of the invention provide a therapeutic platform that leverages the synergistic potential of narrative therapy and narrative neuroscience.

Upon entering a designated monitored area, in an exemplary implementation the individual would be exposed to an environment where ambient light plays a crucial role in association with the exposure to psychoactive therapies. This light is not merely for illumination but forms an integral part of the communication aspects associated with the system. In an exemplary embodiment, the room is equipped with advanced light-based interfaces, such as Light Fidelity (Li-Fi) and optogenetic neural modulation devices, which can transmit and receive information through light signals. Li-Fi leverages the high-frequency modulation of light to provide faster communication. In this therapeutic context, Li-Fi is utilized to create a bidirectional communication channel between the user 2090 and the system, enabling real-time monitoring of the user's 2090 responses to the therapy and facilitating immediate adjustments to the treatment protocol. Optogenetic neural modulation devices are another key component of the advanced light-based interfaces. These devices use light to control neurons that have been genetically modified to be light-sensitive, allowing for the precise manipulation of neural circuits. By integrating optogenetics into the therapeutic environment, the system can directly modulate brain activity in response to the user's 2090 emotional and cognitive states, as detected by the central processing unit. These interfaces are connected to a central processing unit that interprets the light signals as data inputs and outputs. The central processing unit serves as the brain of the therapeutic environment, interpreting the light signals emitted and received by the Li-Fi and optogenetic devices. It processes these signals as data inputs, which inform the system's understanding of the user's 2090 current state, and as data outputs, which guide the system's therapeutic interventions. The central processing unit employs algorithms to analyze the incoming data and to generate appropriate light-based responses that support the user's 2090 therapeutic journey. In embodiments, the designated monitored area is further enhanced to incorporate advanced lighting systems that utilize the principles of lithography and EUV light sources. These technologies are integrated into the therapeutic environment to achieve precise control over the light spectrum and intensity, thereby contributing to the therapeutic efficacy of the system. Lithography, a process traditionally associated with semiconductor manufacturing, involves the transfer of patterns onto a substrate. In this therapeutic setting, lithography techniques are repurposed to create intricate light patterns that can influence neural activity. The system employs microscale lithographic tools to shape the ambient light into specific configurations that are designed to interact with the user's 2090 neural pathways in a targeted manner. Near-infrared (NIR) light, characterized by its deeper tissue penetration and safety profile, offers a high degree of precision and is used to modulate the therapeutic light environment with significant accuracy. NIR sources within the room can be tuned to emit light at specific wavelengths known to affect brain function, thereby enhancing the system's ability to induce desired psychological states or to support cognitive processes.

In embodiments of the invention, technologies mentioned herein, including those such as high-resolution neuroimaging, machine learning algorithms, and data analytics are harnessed to create a virtual twin of the user's 2090 brain—a digital model that mirrors the user's 2090 unique neural architecture and activity patterns. This virtual twin in accordance with the preferred embodiment is constructed by aggregating and analyzing vast amounts of data from various sources, including EEG, fMRI, and other biometric sensors, which capture the electrical and functional dynamics of the brain in real-time. Machine learning algorithms process this data to identify and map networks of neural connections and the flow of information within the brain. The resulting virtual twin serves as a foundational element of the user representation, providing an in-depth, dynamic profile of the user's 2090 cognitive and emotional states. This digital twin enables the system to simulate and predict the user's 2090 responses to different therapeutic interventions, allowing for the personalization of therapy at an extremely high level of accuracy and specificity, ultimately enhancing the efficacy of the therapeutic process in accordance with the preferred embodiment.

In an exemplary implementation of the virtual twin of the brain, the system employs holographic brain imaging to elevate the user representation 3000 providing interactivity and precision. Utilizing neuroimaging techniques such as MRI and fMRI, the system constructs a three-dimensional model of the patient's brain. This model captures the structures and functional areas, pinpointing regions that are critical for the therapeutic process. The data from the 3D brain model created in accordance with an embodiment is then transformed into holographic data through computational methods. This data serves as the blueprint for generating a holographic image of the patient's brain, which can be projected and manipulated in a three-dimensional space. The holographic brain model not only provides a visually compelling representation of the patient's neural activity but also allows clinicians and patients to interact with the model in real-time, offering an immersive way to visualize and understand the brain's response to therapy. This holographic visualization is presented in an embodiment as the virtual twin of the brain, enhancing the system's ability to simulate, analyze, and optimize therapeutic interventions tailored to the patient's neural landscape.

Figure 3:
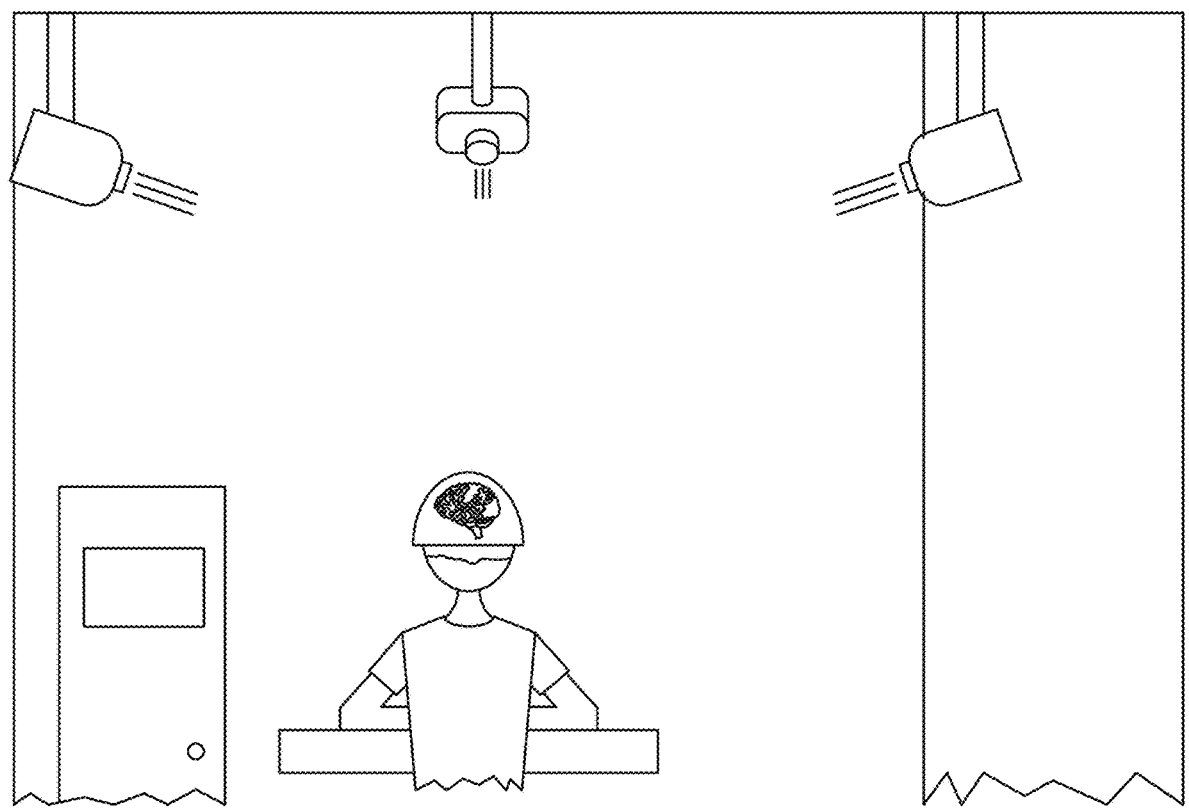
FIG. 3 depicts an intended physical environment during an intended utilization by a user and aspects of the holographic projection system in accordance with an exemplary embodiment.

An embodiment incorporates a holographic projection system 140, in one aspect designed to present the virtual twin of the brain 150 within the therapeutic environment, as depicted in FIG. 1 and FIG. 3. The holographic projection system in an exemplary implementation utilizes holographic lenses 155, which are specialized optical elements capable of diffracting light to form a three-dimensional image of the brain 150 as appearing in the space surrounding the patient. These lenses 155 are engineered to focus and direct the holographic data with high fidelity, ensuring that the projected brain image 150 approximates a true spatial representation of the patient's brain model.

To achieve dynamic control over the holographic projection, the holographic projection system in an embodiment employs Spatial Light Modulators (SLMs). SLMs are devices that manipulate light waves to alter their phase and amplitude, which is essential for the accurate rendering of holographic images. By adjusting these properties of light, the SLMs can modify the holographic projection in real-time, allowing for interactive visualization that responds to changes in the patient's neural activity or to different stages of the therapeutic process.

For instance, the holographic projection system might utilize a liquid crystal on silicon (LCoS) Spatial Light Modulator (SLM), renowned for its high-resolution modulation capabilities and prevalent use in holographic displays. In one embodiment of the invention, the LCOS SLM is coupled with a Fourier lens, which effectively transforms the holographic data into a detailed 3D projection, enhancing the depth and clarity of the holographic images. Alternatively, the holographic projection system may employ a Digital Micromirror Device (DMD) as the SLM. The DMD comprises an array of microscopic mirrors, each capable of independent tilting, allowing for precise manipulation of light reflection. This setup enables the DMD to dynamically adjust the amplitude, phase, or direction of the incoming light beam, which is crucial for creating and modifying holographic patterns in real-time. The rapid switching capabilities of each micromirror in the DMD facilitate high refresh rates and meticulous control over the intensity and direction of the projected light, making it exceptionally suitable for applications that demand quick alterations in holographic content or require precise light manipulation. This versatility allows for the creation of highly dynamic and precise holographic displays, suitable for a range of therapeutic and diagnostic applications. . . . By integrating such technologies, the holographic projection system in an embodiment not only visualizes the brain's structure but also its functional activity, such as blood flow changes during fMRI, in a dynamic and interactive manner. This visualization allows clinicians and others to observe and interpret the patient's brain activity patterns with an unprecedented level of detail and provides patients with a tangible, intuitive understanding of their own neural processes, thereby enhancing the overall efficacy and experience of the therapeutic intervention in accordance with the preferred embodiment.

An embodiment of the invention incorporates an array of light sources, in association with the holographic projection system or another aspect of the embodiment of the invention, to provide a highly specialized and personalized therapeutic experience. The light sources, which may include lasers and LEDs, are configured to emit light at specific wavelengths and intensities that are known to have therapeutic effects on neural tissue. These light sources are programmable and can be adjusted to deliver light therapy that is tailored to the individual therapeutic requirements of the patient. An embodiment of the invention incorporates an array of light sources, in association with the holographic projection system or another aspect of the invention, to provide a highly specialized and personalized therapeutic experience. The light sources, which may include lasers and LEDs, are configured to emit light at specific wavelengths and intensities that are known to have therapeutic effects on neural tissue. These light sources are programmable and can be adjusted to deliver light therapy that is tailored to the individual therapeutic requirements of the patient. The programmability of the light sources allows for the precise control of light parameters, including wavelength, intensity, pulse duration, and modulation frequency, which can be optimized based on the patient's response to therapy. This customization is critical, as different neural tissues may respond to different light characteristics. The light is projected through a mask, which represents the desired pattern of neural stimulation or inhibition, and an intricate system of lenses that shrink and focus the pattern onto the brain's surface with microscale precision. This level of precision enables the targeting of light at a resolution fine enough to affect specific neural pathways without impacting surrounding tissues. The targeted interaction of shaped light with neural tissue has been found by the inventor to influence neural activity in a controlled manner. Depending on the wavelength and intensity, the light could activate or inhibit neuronal firing, modulate neural networks, and promote neuroplasticity. For instance, blue light might be used to excite specific neurons, while red or near-infrared light could be used to reduce inflammation or promote healing. The invention's ability to shape and direct light with such precision opens up new possibilities for non-invasive neural modulation, offering a potential treatment for a variety of neurological conditions without the need for pharmacological interventions.

The dynamic targeting capability distinguishes the preferred embodiment from conventional light therapy methods. By integrating the holographic projection system with the array of light sources, an embodiment of the invention can direct therapeutic light with high precision to specific regions within the holographic brain representation. This is achieved by synchronizing the light sources with the spatial coordinates of the holographic image, allowing for targeted stimulation or modulation of neural activity in areas of interest, such as regions implicated in mood regulation or cognitive function.

In an exemplary embodiment, the system incorporates a laser diode that emits light in the near-infrared spectrum to target the prefrontal cortex within the holographic brain model, aiming to modulate activity in this region which is often associated with depression. The intensity, pulsing frequency, and duration of the light therapy are controllable in real-time in accordance with an embodiment, based on feedback from the patient's virtual brain twin, ensuring that the therapy is delivered with optimal timing and dosage.

Furthermore, the system's dynamic targeting is not limited to static points within the brain model; it can also track and adjust to changes in the holographic projection, such as shifts in the representation of neural activity during the therapy session. This allows the light therapy to be responsive to the evolving therapeutic needs of the patient, providing a responsive and adaptive treatment modality.

An embodiment provides for real-time feedback and control to enhance the adaptability and efficacy of the therapeutic system. In accordance with an embodiment, this is achieved through continuous monitoring of the patient's brain activity using non-invasive neuroimaging techniques such as electroencephalography (EEG) or functional magnetic resonance imaging (fMRI). These techniques provide a real-time stream of data reflecting the electrical or hemodynamic changes in the brain as the patient undergoes therapy.

An embodiment incorporates control algorithms that are designed to interpret the data obtained from brain activity monitoring. These algorithms analyze patterns and fluctuations in neural signals to assess the patient's response to the therapy. Based on this analysis, the algorithms dynamically adjust the parameters of the holographic projection and the targeted light therapy. For example, if EEG monitoring reveals increased alpha wave activity in a region targeted for relaxation, the control algorithms may modulate the intensity or wavelength of the light therapy to enhance this effect.

The adaptive control system operates in a closed-loop manner, where the output (holographic projection and light therapy) is continually adjusted based on the input (real-time brain activity data). This ensures that the therapeutic interventions are fine-tuned to the patient's current state, providing a personalized treatment protocol that can evolve with the patient's progress. The system's ability to respond to changes in brain activity in real-time allows for the optimization of therapy, potentially improving outcomes by delivering the right therapeutic intervention at the right time.

The person's brain activity in an exemplary implementation is monitored using non-invasive brain-computer interface (BCI) technologies, such as electroencephalography (EEG), which detect the electrical patterns associated with cognitive processes and emotional states. When psychedelic compounds are administered during an intended use associated with the invention, the person subjected to the psychedelic compounds experiences more fluid and expansive state of consciousness, potentially enhancing the person's brain's ability to generate unique electrical patterns that correspond to the individual's internal experiences.

Aspects of embodiments of the invention presented herein and the associated methods are directed to interpreting brain activity through the analysis of electrical waveforms obtained from an electroencephalogram (EEG), which offers several advantages. By processing and decoding these waveforms, the system can infer specific cognitive states, mental processes, responses to stimuli, and one or more neural units of the patient associated with specific semantic meaning. This approach provides a direct link between the physiological activity of the brain and the psychological experiences of the patient, enabling a more nuanced understanding of the patient's mental state.

One of the primary advantages of using EEG to interpret brain activity is the non-invasive nature of the technology. EEG involves placing electrodes on the scalp, which can detect the brain's electrical fluctuations without any need for surgical intervention. This makes it a safe and repeatable method for monitoring brain activity over time, which is particularly beneficial for longitudinal studies and ongoing therapeutic applications.

Another advantage is the temporal resolution that EEG offers. EEG can capture the brain's electrical activity in real-time, allowing for the observation of dynamic changes in brain states. This is particularly important in therapeutic settings where immediate responses to stimuli or interventions are critical for patient care and for adjusting therapeutic strategies.

The system processes the EEG waveforms using advanced signal processing algorithms that can distinguish between different types of brain waves, such as alpha, beta, delta, and theta waves. Each type of wave is associated with different states of consciousness and cognitive processes. For example, alpha waves are typically associated with a state of relaxation, while beta waves are linked to active thinking and focus.

Machine learning models are employed to decode the EEG waveforms into meaningful cognitive states or semantic meanings. These models are trained on datasets that correlate specific waveform patterns with known cognitive states or language elements. The training process involves exposing the system to a variety of brain states and the corresponding EEG data, allowing the system to learn the patterns associated with each state.

The ability to infer cognitive states from EEG data has significant therapeutic implications. For patients with communication difficulties, such as those with aphasia or in a minimally conscious state, the system can provide a means of understanding their responses to stimuli or their unspoken needs. In the context of psychedelic therapy, where patients may have difficulty articulating their experiences, the system can offer insights into the profound cognitive and emotional states induced by these compounds.

The association of neural units with specific semantic meanings is another innovative aspect of embodiments of the invention including the associated methods. By identifying the neural correlates of language, the system can facilitate communication with patients who are unable to speak or write. This can be achieved by translating the EEG data into a synthetic speech or text output, providing a voice for those who otherwise would not be able to express themselves.

The default mode network (DMN) is a network of interacting brain regions that is active when an individual is not focused on the outside world and the brain is at wakeful rest, such as during daydreaming, mind-wandering, and introspection. It involves areas of the brain such as the medial prefrontal cortex, posterior cingulate cortex, and adjacent precuneus, along with parts of the inferior parietal lobe. The DMN is associated with self-referential thought processes, including self-identity, recall of personal memories, and contemplation of one's own emotions and the emotions of others. It is thought to contribute to the maintenance of one's sense of self and the continuity of one's background mental 'narrative'. The activity within the DMN is often reduced during focused tasks and is also affected by the use of psychedelic compounds, which can lead to an altered sense of self and a feeling of connectedness with the external world.

The phenomenon of a more fluid and expansive state of consciousness during the utilization of psychedelic compounds is characterized by a significant increase in the brain's neuroplasticity and a decrease in the default mode network's activity, which is often associated with self-referential thoughts and a sense of ego. The compounds, such as psilocybin, LSD, or DMT, act on specific serotonin receptors, which can lead to a cascade of changes in brain activity and connectivity. As a result, those individuals receiving such psychedelic compounds may experience a dissolution of their normal sense of self and a heightened state of sensory and emotional awareness. These altered states are accompanied by unique electrical patterns in the brain, as evidenced by EEG readings that show distinct waveforms not typically present during ordinary consciousness. These patterns are believed to correspond to the rich inner experiences reported by individuals, such as synesthetic perceptions, deep emotional breakthroughs, and profound insights. In an embodiment, the present invention harnesses these unique electrical patterns, using them as a basis for a novel communication system that translates these internal experiences into an external, interpretable form. By doing so, the preferred embodiment provides a means for individuals to convey the essence of their psychedelic experiences, which are often challenging to articulate, thereby enabling a deeper understanding and integration of these transformative states.

A processor forms an integral aspect associated with embodiments of the invention. In the preferred embodiment, the processor aspect comprises a central processing unit (CPU) as a critical component. The CPU, appreciated by those skilled in the art as the brain of the computer, is responsible for executing program instructions and managing the data flow between various parts of the system. In the context of the preferred embodiment, the CPU is tasked with the complex processing of multi-modal data inputs, such as EEG signals, audio, visual, and textual data, which are integral to the system's functionality. In exemplary implementations, the CPU utilizes advanced algorithms, including machine learning and neural networks, to analyze and interpret the user's 2090 emotional and physiological states. The CPU's processing power enables real-time analysis and feedback, ensuring the system's adaptive digital therapy is responsive and personalized. Examples of CPUs that could be employed in this system include, but are not limited to, high-performance microprocessors from the Intel Xeon or AMD EPYC series, which offer the necessary computational capabilities to handle the intensive data processing required by the system. These CPUs are capable of parallel processing and can be integrated with specialized hardware accelerators, such as GPUs or FPGAs, to further enhance the system's ability to perform complex neural network computations and real-time data analysis. In association with exemplary uses, embodiments of the invention are performed in association with in person, computer-aided and/or application-driven therapy sessions, such as those described in U.S. Pat. No. 11,810,337 issued on Nov. 7, 2023, which is hereby incorporated by reference in its entirety.

Electroencephalography (EEG) is a non-invasive method used to record electrical activity of the brain. It involves the use of sensors, known as electrodes, which are placed on the scalp to detect the brain's electrical fluctuations resulting from ionic current flows within the neurons of the brain. In other contexts, this technology is crucial for monitoring brain states, diagnosing conditions like epilepsy, and for research into brain-computer interfaces. In the context of embodiments of the present invention, EEG data serves as a primary input for assessing the user's 2090 emotional and physiological states, particularly when influenced by psychedelic compounds. The EEG captures the unique electrical patterns associated with the user's 2090 altered state of consciousness, which the system's processor then decodes and translates into communicable data.

An Ambulatory EEG is a portable version of the EEG system that allows for continuous brain activity monitoring over extended periods, typically ranging from 24 hours to several days, while the user 2090 is mobile and engaging in normal daily activities. This device is particularly useful in the context of embodiments of the invention as it enables the collection of EEG data in a variety of settings, including non-clinical environments where users may be experiencing the effects of psychedelic compounds. The Ambulatory EEG ensures that the system can capture a comprehensive dataset of the user's 2090 brain activity as they interact with the environment, which is essential for the adaptive feedback loop described in the invention.

In association with an exemplary implementation of the invention, models of EEG and Ambulatory EEG systems that could be used include the Emotiv EPOC+ for its high-resolution brain wave data and user-friendly interface, and the BioSemi ActiveTwo system, which is known for its research-grade data quality and flexibility in electrode placement. These models are equipped with multiple channels that can provide detailed and robust data streams, ensuring that the system can accurately capture the complex patterns of brain activity induced by psychedelic compounds. In an exemplary implementation, the data from these EEG systems would be fed into the central processing unit, which would apply advanced algorithms to interpret the signals and facilitate the real-time communication and therapeutic feedback mechanisms associated with embodiments of the invention.

The central processing unit associated with the preferred embodiment receives the EEG data and employs machine learning algorithms to decode the electrical signals into meaningful information. This information is then mapped onto a neural library, which comprises a database of known patterns and their associated semantic meanings. The concept of a neural library within the context of an embodiment of the invention refers to a comprehensive database, in communicative linkage with other aspects of the invention including but not limited to a computer processor and machine learning aspects, that stores a vast array of neural response patterns and their corresponding semantic meanings. This library acts as a repository of the electrical signatures associated with specific cognitive and emotional states, as well as the linguistic and symbolic representations that individuals use to express these states. Neural response patterns and their corresponding semantic meanings are captured using EEG technologies by recording the electrical activity generated by the brain. EEG devices consist of multiple electrodes placed on the scalp that detect the brain's electrical signals. These signals are the result of synaptic activity and neuronal firing patterns that occur as the brain processes information and responds to stimuli. When a person thinks, feels, or performs a task, specific regions of the brain are activated, and this activity can be observed as changes in the EEG signal. For instance, certain thought processes or emotional states may produce characteristic waveforms or oscillatory patterns that can be detected by the EEG electrodes. These patterns are then digitized and analyzed using signal processing techniques to extract meaningful information about the underlying brain activity. When the system captures EEG data or other inputs indicative of a user's 2090 internal experience, particularly in altered states of consciousness induced by psychedelic compounds, this information is compared against the patterns stored in the neural library.

In association with an exemplary embodiment, machine learning algorithms, including supervised learning techniques, can then be used to create models that map these neural response patterns to their semantic meanings. The models are trained on datasets where the semantic context is known, allowing the algorithm to learn the association between the EEG patterns and the corresponding semantic content. Once trained, these models can be used to interpret new EEG data in real time, providing insights into the user's 2090 mental state and facilitating communication or therapeutic interventions based on the user's 2090 cognitive or emotional condition. The collection of these associations forms the basis of the neural library, which serves as a reference for understanding and interacting with the brain's complex signaling language.

In embodiments of the invention, the neural library is constructed through the aggregation and analysis of extensive EEG and other biometric data collected from multiple individuals over time. Machine learning algorithms are employed to identify and categorize the unique electrical patterns associated with various thoughts, feelings, and experiences. Each identified pattern is then linked to its semantic equivalent, creating a rich lexicon of brain activity that can be referenced by the system.

In practice, when a user's 2090 data is processed by the system, the neural library enables the identification of specific mental states by matching the incoming data with the pre-established patterns. This allows the system to interpret the user's 2090 experience with a high degree of accuracy and to provide feedback or generate communications that are tailored to the user's 2090 current state. The neural library is continually updated and refined as new data is collected, enhancing the system's ability to understand and interact with the user's 2090 unique neurological language. This dynamic and evolving database is fundamental to the invention's ability to facilitate effective two-way communication between the user 2090 and the therapeutic system.

In the context of the preferred embodiment of the invention, the collected neural library, which comprises neural response patterns and their corresponding semantic meanings, serves as a foundational element for translating brain activity into communicable language. This translation process begins with the EEG technologies capturing the electrical activity of the brain, which reflects the user's 2090 cognitive and emotional states. The recorded EEG signals are then analyzed and matched against the pre-established patterns stored within the neural library. Through the use of machine learning models, these patterns are associated with specific semantic meanings, effectively decoding the electrical signals into a language that can be understood. The system then utilizes this decoded information to generate appropriate communicative outputs, such as text, audio, or visual signals, which are tailored to the user's 2090 current state. This enables a dynamic and interactive exchange between the user 2090 and the system, facilitating a form of communication that is informed by the direct neural responses of the user, thereby enhancing the therapeutic process and providing a personalized experience.

Figure 6:
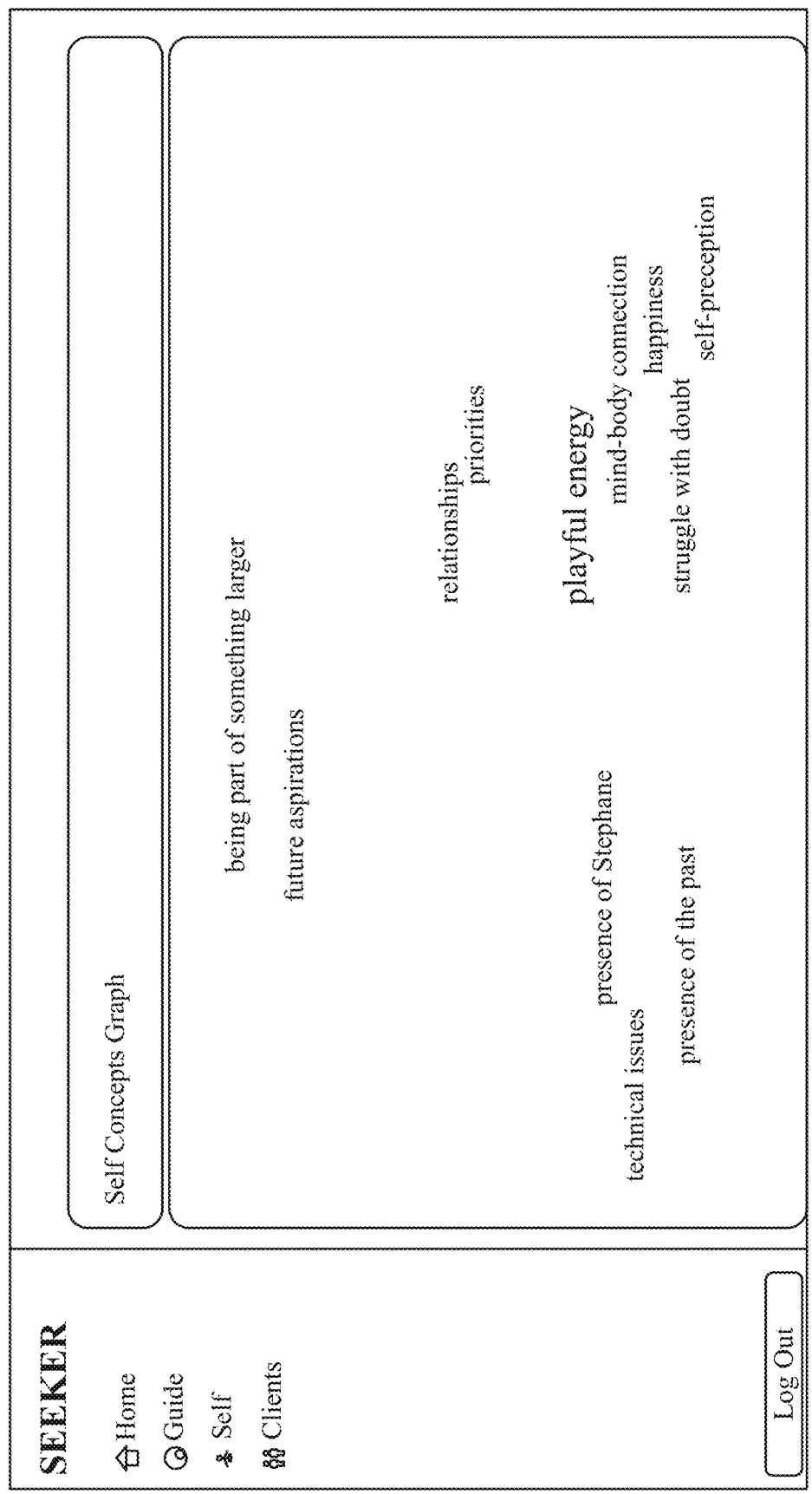
FIG. 6 depicts a self-concepts user interface in accordance with an exemplary embodiment.
Figure 8:
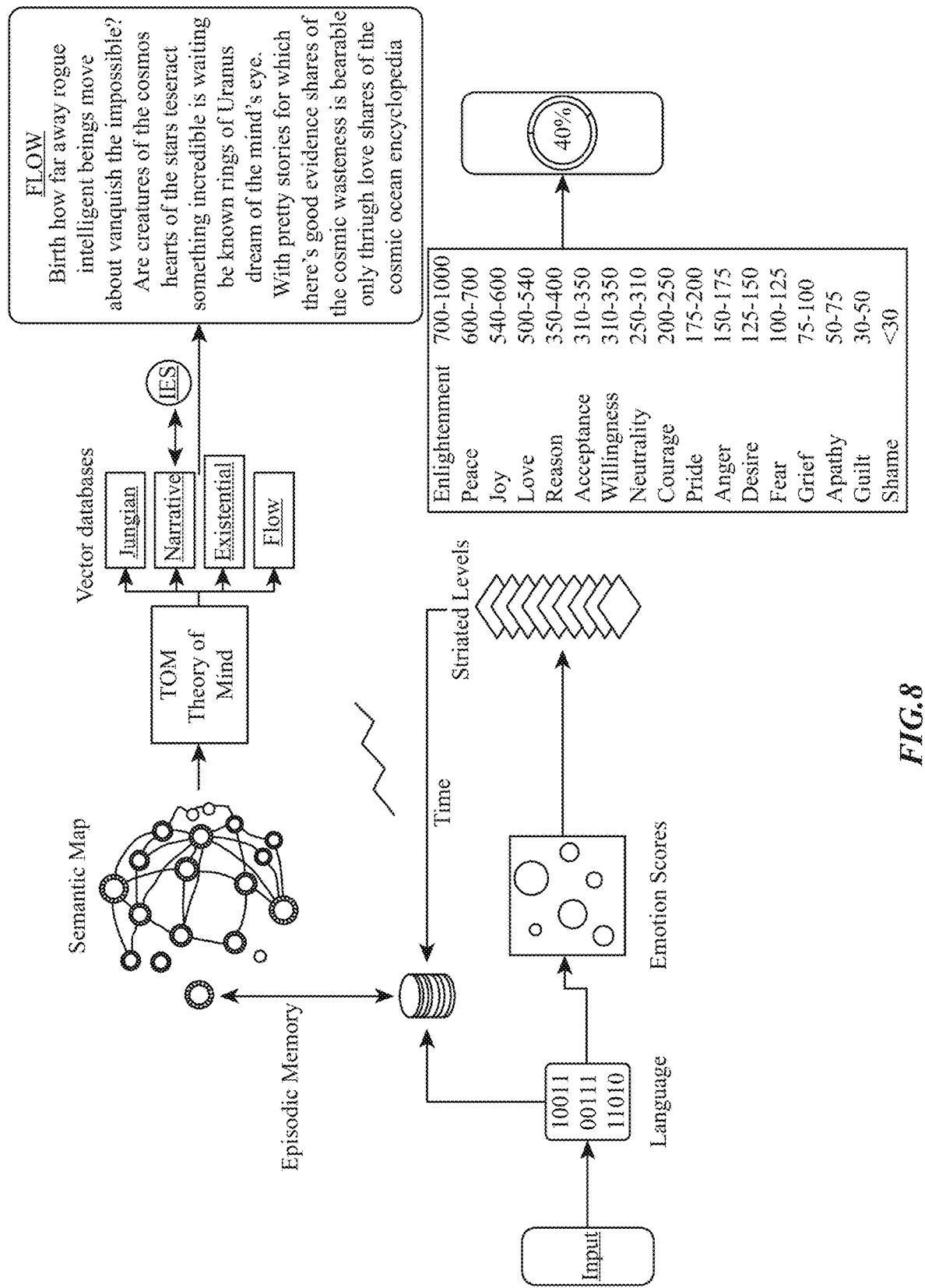
FIG. 8 depicts a schematic of the system in accordance with an exemplary embodiment.

In an embodiment, it is an aspect of the invention to provide for the definition of communication language through text. The ability to generate text-based communication is an essential aspect providing for the system's ability to interact with the user 2090 in association with an embodiment. Text-based communication is enabled by converting the user's 2090 neural response patterns, as captured by EEG and other biometric sensors, into written language. This process begins with the system's algorithms analyzing the EEG data to identify specific brainwave patterns that correlate with the user's 2090 thoughts and emotions. These patterns are then cross-referenced with the neural library, which contains a vast array of neural signatures and their associated semantic meanings. Once a match is found, the system translates these meanings into text messages, which can be displayed on a self-concepts user interface as depicted in an exemplary embodiment by FIG. 6, or communicated through other text-based channels. This text could take the form of words, sentences, or even complex narratives that reflect the user's 2090 internal state or intended message, as depicted in an exemplary embodiment in FIG. 6. The system is designed to learn and adapt over time, improving its ability to accurately translate neural activity into text as more data is collected and the neural library is expanded. This text-based communication allows for a nuanced and precise method of interaction that can be easily integrated into digital therapeutic environments, providing users with feedback, guidance, or therapeutic content in a format that is both familiar and accessible.

It is likewise an aspect of embodiments of the invention to provide for defining communication language through audio. This aspect involves the transformation of neural response patterns into auditory signals that can be perceived and understood. This auditory communication is facilitated by first capturing the user's 2090 brain activity via EEG and other biometric sensors, which monitor the electrical patterns associated with cognitive processes and emotional states. These patterns are then processed and interpreted using advanced algorithms that reference the neural library which comprises a database containing the correlations between neural signatures and their semantic meanings. When a neural pattern indicative of a particular thought or emotion is identified, the system in one aspect translates this information into an audio message. This could be in the form of spoken words, generated by text-to-speech technologies, or other auditory cues such as tones or music that convey the intended message or emotional tone. The audio output is then delivered to the user 2090 through speakers or headphones, providing real-time feedback or therapeutic guidance. The system's ability to convert complex neural data into audio communication allows for an interactive and immersive experience, which can be particularly beneficial in therapeutic settings where verbal engagement and auditory processing are integral to the treatment process. As the system continues to learn from each relevant interaction, it refines its capacity to deliver precise and meaningful audio communications that are tailored to the individual needs and responses of the user.

Another aspect of an embodiment is to provide for communication defined through symbols and/or symbolic language. This aspect involves the interpretation and representation of neural response patterns using symbols or imagery that convey specific meanings or concepts. The associated process begins with the collection of EEG data and other biometric information that reflects the user's 2090 mental and emotional states. These data are analyzed by the system's algorithms, which draw upon the neural library to match the detected brain activity patterns with their associated semantic meanings. Once a relevant neural pattern is identified, the system translates this pattern into a symbolic representation. In various exemplary implementations, these symbols could be icons, pictograms, or other visual elements that are universally recognized or have been specifically designed to represent particular emotions, ideas, or instructions. In association with embodiments of the invention, the chosen symbols are then presented via a visual interface, such as a computer screen, mobile device, or augmented reality display. The use of symbolic language allows for a form of communication that can transcend linguistic barriers and can be particularly effective in conveying complex concepts or emotions quickly and intuitively. This method of communication is especially useful in therapeutic settings where verbal communication may be limited or where visual symbolism can have a profound impact on the user's 2090 understanding and emotional well-being. The system's capacity to accurately convert neural signals into symbolic language enhances the user's 2090 ability to interpret and interact with the therapeutic content, facilitating a more engaging and personalized therapeutic experience.

An embodiment incorporates the capability to interpret and represent neural responses via an image analysis module designed to delve into the visual contents of the brain. This module utilizes advanced pattern recognition algorithms to identify and record images that the user's 2090 brain activity may suggest, focusing on symbols that are often universal in nature and recurrent in various forms of religious and spiritual imagery, such as mandalas. Such symbols are typically geometric or fractal, reflecting a deep-seated archetypal language that resonates across different cultures and belief systems.

In accordance with an embodiment, algorithms are trained to recognize these archetypal patterns and decipher their symbolic meanings, translating the neural language of the subconscious into a visual lexicon akin to hieroglyphs. This process not only captures the essence of the user's 2090 inner experiences but also seeks to uncover a cohesive language that maps the user's 2090 journey through the therapeutic process. By identifying recurring motifs and symbols within the user's 2090 neural imagery, the system constructs a narrative that mirrors the individual's psychological and emotional trajectory. Thus, such embodiment provides insights into the subject's inner world.

The resulting symbolic representations are then integrated into the therapeutic interface in an embodiment. There, the symbolic representations serve as visual anchors for the user's 2090 experiences, facilitating comprehension and reflection. This approach in an embodiment allows the subject user 2090 to engage with their subconscious in a more direct and meaningful way. The present inventor has found that the embodiment thus promotes a deeper understanding of the subject user's 2090 inner self, thereby supporting the therapeutic goals of self-discovery and personal growth. Through this use of symbolic language in accordance with an embodiment, the invention provides a powerful tool for enhancing the efficacy of therapeutic interventions and fostering transformative experiences.

In association with an embodiment, the system provides for communication defined through electrical signals. In an aspect, communication through electrical signals involves the direct translation of neural activity into electrical patterns that can be transmitted and interpreted as meaningful communication. This process starts with the collection of neural data, primarily through EEG, which records the electrical activity of the brain as it responds to various stimuli or internal states. Aspects of the system interpret the electrical signals as indicative of the user's 2090 cognitive and emotional processes and are processed by the system to identify distinct patterns that correspond to specific thoughts, emotions, or intentions. In an exemplary embodiment, such aspects are designed to interpret electrical signals from the user's 2090 brain, as captured by EEG and other biometric sensors, to discern cognitive and emotional processes.

Algorithms associated with the system process these signals to detect distinct neural patterns, which are then matched with a neural library of known patterns correlated with specific thoughts, emotions, or intentions. This matching process enables the system to translate the user's 2090 neural activity into actionable data, which can be communicated back to the user 2090 or to clinicians in a meaningful way, facilitating real-time monitoring and adaptive responses within the therapeutic context. The algorithms integral to the system employ machine learning techniques, including deep neural networks and pattern recognition algorithms, to analyze the electrical signals obtained from the user's 2090 brain activity. These algorithms are trained on extensive datasets that include a wide range of neural patterns and their associated cognitive and emotional states. By comparing incoming EEG signals against this neural library, the algorithms can identify specific neural signatures that correspond to known thoughts, emotions, or intentions. For instance, a particular pattern of brain waves might be recognized as indicative of stress or relaxation, and the system would match this pattern to its corresponding state in the neural library.

Embodiments of the invention incorporate aspects directed to machine learning and machine learning models. In an embodiment, a machine learning model utilized in association with the invention mirror human cognition by adhering to the theoretical frameworks of Convergence-Divergence Zones (CDZs) as proposed by Antonio Damasio and Intrinsically Motivated, Curiosity-Driven Learning as outlined by Simon Kaplan and Pierre-Yves Oudeyer. These models are designed to closely follow and replicate the processes underlying human thought, learning, and decision-making.

Convergence-Divergence Zones Framework Implementation:

In line with Damasio's Convergence-Divergence Zones framework, the machine learning models within the system are structured to simulate the integration and differentiation of neural signals that occur in the human brain. These models are enabled to identify patterns in sensory inputs and cognitive processes, converging this information to form coherent representations of concepts or experiences. Subsequently, they can diverge this information to generate multiple potential outcomes or interpretations, akin to the brain's ability to extrapolate and imagine based on past experiences.

The system's architecture allows for the continuous adaptation of these models as they encounter new data, reflecting the brain's capacity for learning and neural reorganization. By simulating the convergence and divergence of information, the models can support the user 2090 in recognizing and restructuring cognitive schemas during therapeutic interventions, particularly within the identified neuroplastic windows.

Intrinsically Motivated, Curiosity-Driven Learning Framework Application:

In an embodiment, the machine learning models embody principles of Intrinsically Motivated, Curiosity-Driven Learning, as they are programmed to seek out novel patterns and anomalies in the data that may indicate a departure from established cognitive schemas. This approach fosters a system that is inherently curious and motivated to explore the user's 2090 cognitive landscape, promoting the discovery of new insights and the development of personalized therapeutic content.

By implementing this learning framework, the system encourages users to engage with unfamiliar or challenging experiences that can stimulate cognitive growth. The models prioritize user engagement and reward the exploration of new cognitive territories, thereby facilitating the intrinsic motivation that drives curiosity and learning in humans.

The synergy between the machine learning models and human cognition in association with exemplary uses of the system is further enhanced by the system's ability to process complex emotional and cognitive data in real-time. The machine learning models in an embodiment are trained on diverse datasets that include not only objective measures of brain activity but also subjective reports of user experiences and emotional states. This comprehensive approach ensures that the models can accurately reflect and support the nuanced nature of human cognition.

Aspects of the present invention draw inspiration from the field of developmental robotics, which seeks to understand the complexities of the brain by attempting to replicate its functions within robotic systems. This approach is grounded in the philosophy of "building the brain" to gain deeper insights into its developmental processes. In the context of the invention, this translates into the creation of machine learning models that can learn and adapt in a manner akin to a developing human brain, continuously refining their understanding of sensory-motor and symbolic information.

To emulate the layered structure of the brain, in an embodiment, the system employs hierarchical multimodal self-organizing maps (HSOMs) that can represent various levels of sensory-motor and symbolic information. These maps are designed to self-organize based on input data, creating a structured representation of the user's 2090 sensory experiences and cognitive processes. HSOMs can capture the intricate relationships between different modalities of information, such as visual, auditory, and tactile inputs, and how they relate to motor outputs and symbolic thought.

In the developmental robotics context, HSOMs have been utilized to enable robots to learn from their bodies and environments autonomously. Similarly, in association with embodiments of the present invention, HSOMs allow the system to learn from the user's 2090 physiological and psychological data, creating a dynamic model that reflects the user's 2090 evolving cognitive and emotional state.

The system's machine learning models incorporate principles of embodied learning, where the acquisition of knowledge is grounded in the user's 2090 physical experiences and interactions with their environment. By processing data from the user's 2090 movements, gestures, and environmental responses, the models can develop a more holistic understanding of the user's 2090 behavior and its cognitive underpinnings.

This approach mirrors the way developmental robotics systems learn from sensorimotor experiences, gradually building more complex representations of the world and their interactions with it. The system's models are thus capable of simulating the developmental trajectory of human learning, from basic sensorimotor coordination to advanced symbolic reasoning.

The system's machine learning models are adaptive, capable of not only learning from the user's 2090 current state but also predicting future cognitive and emotional developments. This predictive ability is crucial for identifying the optimal timing for therapeutic interventions during neuroplastic windows. By anticipating changes in the user's 2090 cognitive schema, the system can proactively adjust its therapeutic strategies to support the user's 2090 ongoing development.

The developmental robotics-inspired machine learning models are intrinsically designed to support the user's 2090 cognitive growth, providing a scaffold that evolves as the user's 2090 understanding and emotional well-being expand. This adaptive learning process is central to the system's ability to offer effective, personalized therapy that aligns with the user's 2090 unique developmental path.

Once patterns pertaining to the user 2090 are identified, they are formatted into a standardized electrical signal using a predefined encoding scheme. This encoding scheme translates the neural patterns into a series of electrical impulses that can be easily transmitted and decoded. The formatted electrical signals are then transmitted through appropriate hardware interfaces, which could include direct neural interfaces, brain-computer interfaces (BCIs), or other specialized transmission systems designed to handle bioelectrical communication. In association with an embodiment, upon the identification of neural patterns, the system utilizes one or more of a variety of predefined encoding schemes to transform these patterns into standardized electrical signals. These encoding schemes used in association with varying embodiments may include any of Pulse Code Modulation (PCM), Delta Modulation (DM), or Phase Shift Keying (PSK), or any other encoding scheme capable of translating detected patterns of neural activity into structured electrical impulses that represent the original neural information. For instance, PCM might be used to encode the amplitude of brain waves into a digital signal, while PSK could encode changes in the brain's electrical state into phase changes of a carrier wave, suitable for transmission. These encoded signals are then formatted to adhere to established communication protocols, ensuring seamless transmission through hardware interfaces like direct neural interfaces or brain-computer interfaces (BCIs). For example, a BCI might receive PCM-encoded signals that correspond to a user's 2090 intention to move a limb and translate them into a control signal for a prosthetic device. Alternatively, a direct neural interface could interpret DM-encoded signals that reflect a user's 2090 emotional state and convert them into a visual or haptic feedback, such as changing the color of a wearable LED display to indicate stress levels or generating a specific vibration pattern on a smartwatch to signal a relaxation cue. These interfaces serve as vital links in the bioelectrical communication chain, converting the user's 2090 neural activities into meaningful interactions with therapeutic devices and applications.

For example, consider a user 2090 who is experiencing a moment of joy. In association with an exemplary implementation of the invention, the EEG captures the brain's response, and the system's algorithms identify the neural pattern associated with this emotion. The pattern is then encoded into a specific sequence of electrical pulses. These pulses could be transmitted to a wearable device that the user 2090 is wearing, such as a wristband, which is equipped with actuators that convert the electrical pulses into a gentle vibration pattern. The user perceives this as a physical sensation that corresponds to the emotional state of joy, providing immediate feedback.

In another example, the system might be used in a therapeutic setting where a patient is unable to communicate verbally. The EEG data could reveal neural patterns that the patient associates with specific needs or responses. These patterns are encoded into electrical signals and transmitted to a computer interface. The computer, equipped with a decoding algorithm, interprets the signals and converts them into a visual display or an audible output, such as a synthesized voice that articulates the patient's intent.

In association with various embodiments of the invention, the reception of these electrical signals is important for the system's efficacy. The receiving devices must be calibrated to interpret the electrical signal patterns accurately. In an exemplary implementation, this involves the use of specialized software and hardware that can decode the electrical impulses back into the neural patterns or associated semantic meanings they represent. The system ensures that the transmission of electrical signals is reliable and secure, maintaining the integrity of the communication between the user's 2090 brain activity and the output provided by the system. Thus the preferred embodiment of the invention facilitates a novel form of communication that bypasses traditional sensory channels, offering a direct and potentially transformative way for users to interact with digital therapeutic systems and for clinicians to understand and respond to their patients' needs in real-time.

In association with an embodiment, the system provides for communication defined through visible light. In the preferred embodiment, communication language through visible light provides a non-invasive and intuitive means of interaction with the aid of psychedelics. This aspect of an embodiment the invention is particularly relevant in scenarios where traditional communication methods may be less effective or where the integration of ambient and therapeutic environments is desired.

Light Fidelity (Li-Fi): In an embodiment, Li-Fi technology is integrated into the user's 2090 environment, such as in smart homes or therapy rooms, to create an immersive therapeutic space. The LED lighting in the room could change colors or intensity in response to the user's 2090 emotional state, as detected by the system's sensors and processed by its algorithms. For example, if the system detects signs of anxiety, the lighting could shift to a calming blue, promoting relaxation. This real-time environmental response serves as a form of biofeedback, enhancing the user's 2090 awareness and control over their emotional state.

Optogenetic Neural Modulation: An embodiment incorporates optogenetic techniques as part of a cutting-edge therapeutic protocol. By using light to modulate neural activity, the system can directly influence brain states associated with emotional wellbeing. For instance, during a therapy session, if the system's algorithms determine that the user 2090 would benefit from a reduction in stress, optogenetic neural modulation could be applied to activate neural pathways that induce relaxation. This direct modulation of brain activity could be particularly beneficial in cases where traditional pharmacological or therapeutic interventions are not suitable or have been less effective.

Pulse Code Modulation (PCM): The use of PCM in the context of visible light communication allows for a high degree of precision in transmitting complex emotional data. The system could encode a therapeutic message or emotional state into a PCM signal, which is then transmitted as a sequence of light pulses from a wearable device or therapeutic light source. The user's 2090 device, equipped with a photodetector, decodes the light pulses back into the original message, which could then be displayed as text, images, or used to trigger other therapeutic actions. For example, during a meditation session, the system could transmit PCM-encoded instructions via light pulses to guide the user 2090 through the process, providing a silent and unobtrusive form of guidance.

The integration of visible light communication as an aspect of the invention in an embodiment offers several advantages. It allows for high-speed data transmission in a manner that is inherently secure, as light does not penetrate through walls, ensuring privacy in therapeutic settings. Additionally, it provides a way to leverage the ubiquity of lighting infrastructure for therapeutic purposes, turning everyday environments into potential spaces for emotional wellbeing support. Furthermore, the use of light as a communication medium is inherently safe and does not require invasive procedures, making it an attractive option for users with varying needs and preferences. In association with embodiments, aspects related to visible light communication enhance the system's ability to deliver personalized, adaptive digital therapy, contributing to the user's 2090 emotional wellbeing in a holistic and integrated manner.

In association with various embodiments, communication is facilitated via the transmission of binary packets. These packets, in the preferred implementation, comprise structured collections of bits that represent data in a binary format, which can be transmitted, received, and interpreted by classical computing systems to convey information effectively. With the advent of quantum computing, these constructs may evolve to encompass quantum packets, leveraging the principles of superposition and entanglement to encode and process information more dynamically.

In the context of audio communication, binary packets encode the linguistic content of spoken language. For example, a user's 2090 spoken words are captured by a microphone and converted into digital audio signals using an analog-to-digital converter. These digital signals are then segmented into binary packets—or, in quantum systems, into sequences of qubits. Quantum packets would be transmitted to the quantum processor, which can use quantum algorithms to decode the linguistic and paralinguistic content, extracting meaningful information with potentially greater efficiency and depth due to the inherent parallelism of quantum computing. This quantum-based information could then be used to assess the user's 2090 emotional state with a higher degree of complexity, potentially recognizing subtleties and nuances beyond the capabilities of classical systems.

In providing verbal feedback, in an embodiment a quantum text-to-speech engine converts the system's response into audio signals. The quantum system enables the processing of a vast array of response possibilities simultaneously, selecting the optimal output instantaneously through the collapse of the system's wave function, which determines the state of the qubits at the point of measurement.

Symbolic language communication in the context of an embodiment of the invention involves the use of icons, emojis, or other visual symbols to represent complex ideas or emotions. In an exemplary implementation associated with this modality, each symbol is associated with a unique binary code—or, in the context of quantum computing, a specific configuration of qubits. When a user 2090 selects a symbol on a device interface, a corresponding quantum packet is transmitted to the system. The system decodes the packet to understand the user's 2090 selection and can respond with appropriate symbolic language, such as displaying a sequence of symbols on a screen that guides the user 2090 through a therapeutic exercise. The use of quantum packets allows for a multi-faceted interpretation of data that could account for various probabilistic states of user input, offering a more holistic understanding of the user's 2090 needs and the appropriate feedback. The system's integration with quantum technologies promises advancements in the precision and adaptability of communicative interactions.

Figure 10:
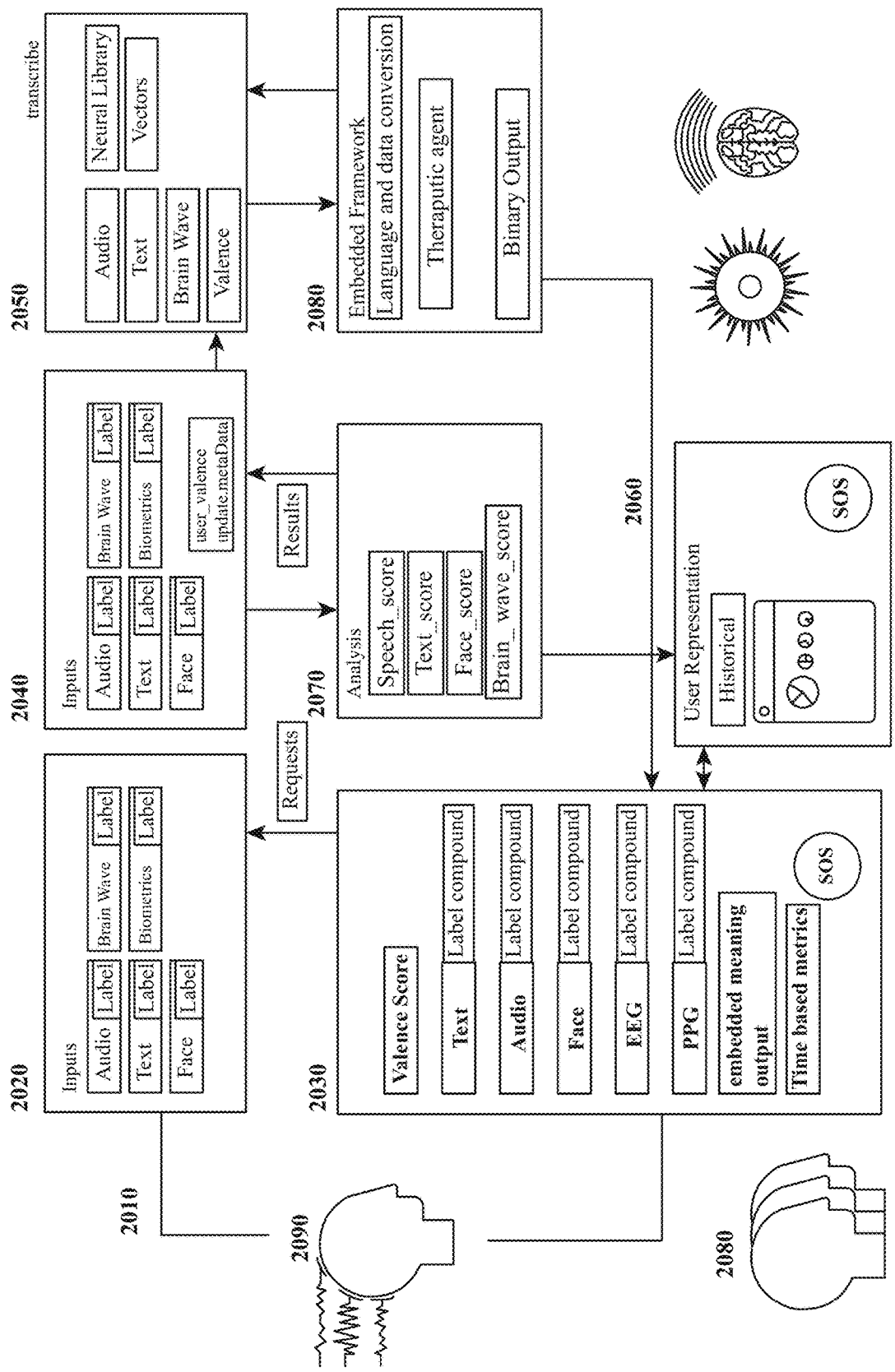
FIG. 10 depicts a schematic of the various components of the system in accordance with an exemplary embodiment.

Communication through electrical signals is particularly relevant in the context of brain-computer interfaces (BCIs) and neural monitoring devices. Here, neural activity is captured as electrical signals, which in an exemplary embodiment are then digitized and formatted into binary packets. These packets contain encoded information about the user's 2090 cognitive or emotional state and are transmitted to the system's processor. The processor decodes the packets, mapping the neural activity to specific mental states or intentions, which can then be used to adjust the therapeutic protocol or to control external devices as part of the therapy. Various processing aspects associated with a processor are represented in an exemplary embodiment as 2070 and 2080 as depicted in FIG. 10, which depicts aspect of the system in an exemplary embodiment.

In another exemplary implementation, binary packets are used to encode information into light signals. For example, using Pulse Code Modulation (PCM), the system in an embodiment converts a therapeutic message into a series of binary packets. These packets are then used to modulate the intensity or color of a light source, such as an LED, in a pattern that represents the encoded message. A photodetector on the user's 2090 device receives the light signals, decodes the binary packets, and translates them back into the original message, which could be displayed as text or used to trigger a therapeutic action, such as changing the ambient lighting to promote relaxation.

In association with each of the preceding examples, the use of binary packets allows for the precise and efficient transmission of complex data. The system's ability to encode and decode these packets across different communication modalities ensures that users can interact with the therapeutic environment in a way that is most comfortable and effective for them, whether that be through speech, symbolic language, direct neural interaction, or the ambient use of light. This flexibility is an aspect of the preferred embodiment of invention, enabling it to cater to a wide range of user needs and preferences while maintaining the integrity of the communicated information.

Various embodiments of the invention comprise an access module. The access module functions as the primary conduit through which user data is collected, processed, and communicated to the rest of the system. It is an integrated hardware and software unit designed to interface with the user 2090 and capture a wide array of expressive and physiological data that reflects the user's 2090 emotional and cognitive states. In association with the preferred embodiment, the access module serves as the primary interface between the user 2090 and the system, acting as a gateway for data collection, processing, and transmission. It is equipped with a variety of interfaces, such as text, audio, symbolic, computer vision, and physiological sensors, including Ambulatory EEG and other biometric devices. The access module is designed to be user-friendly and can be integrated into personal digital devices like smartphones, wearables, or specialized therapeutic equipment.

The hardware associated with an embodiment of the access module includes any of various input devices and sensors in association with embodiments, such as microphones for audio data, cameras for visual data, touchscreens for text and symbolic inputs, and a range of biometric sensors like Ambulatory EEG, fMRI, or wearable devices that measure heart rate, body temperature, and other physiological markers. In an exemplary implementation, the components are engineered to be non-invasive and user-friendly, allowing for seamless integration into the user's 2090 daily life, whether through personal devices like smartphones and smartwatches or specialized therapeutic equipment.

The access module further comprises software aspects. The software within the access module comprises with algorithms and multi-modal models that process the incoming data streams associated with other aspects of the system. In an embodiment, these models can perform tasks such as natural language processing to interpret spoken or written language, computer vision algorithms to analyze facial expressions or gestures, and signal processing techniques to interpret physiological data. In the preferred embodiment, the software is designed to operate in real-time, providing immediate analysis and feedback to the user.

In operation, the access module captures and digitizes the user's 2090 inputs 2020, which are then processed to assess emotional expression and valence. For example, in association with an exemplary implementation, when a user 2090 speaks, the audio is captured by the microphone, converted into digital format, and analyzed for emotional content. Similarly, a camera may capture the user's 2090 facial expressions, which are then processed to infer emotional states. Physiological sensors collect data that is indicative of the user's 2090 internal state, such as stress levels or relaxation.

Once the data is processed, the access module packages the information into binary packets or other suitable data formats for transmission. It then communicates this data to the remote interface, typically via secure wireless communication protocols. This real-time data transfer is critical for the system's ability to provide immediate and adaptive therapeutic interventions.

The access module's real-time processing and communication capabilities are essential for the preferred embodiment of the invention's goal of providing adaptive digital therapy. By continuously monitoring the user's 2090 state and providing feedback or therapeutic content in response, the access module facilitates a closed-loop system that can dynamically adjust to the user's 2090 needs. This personalized approach to therapy, supported by the access module's comprehensive data collection and processing, represents a significant advancement in the field of mental health and emotional well-being support.

Data collected by the access module is diverse, encompassing expressive and physiological inputs 2020 that reflect the user's 2090 emotional and cognitive states. This data is digitized and formatted into binary packets, which may include text transcriptions, audio recordings, symbolic representations, visual data from computer vision interfaces, and raw or processed physiological signals. The access module employs real-time processing to analyze and interpret this data, utilizing multi-modal models to determine the user's 2090 emotional expression and valence.

Once processed, the data is transmitted from the access module to the remote interface in real-time. This transmission can occur over secure wireless communication protocols such as Wi-Fi, Bluetooth, or cellular networks, ensuring that data is relayed swiftly and securely to the remote interface, which may be hosted on cloud servers or on-premises healthcare systems. The real-time aspect is crucial for providing immediate feedback and therapeutic interventions, which is particularly important in the context of mental health and emotional well-being.

Various embodiments of the invention comprise a remote interface. The remote interface in an embodiment comprises a platform that functions as the central hub for the collection, analysis, and interpretation of data transmitted by the access module. In an embodiment, the remote interface consists of an interactive user interface. It is designed to be a secure, scalable, and user-friendly system that clinicians and authorized personnel can access to gain insights into a patient's therapeutic journey, particularly in the context of psychedelic-assisted therapy. Certain embodiments provide platforms for collaborative care, enabling clinicians, therapists, and support networks to access and contribute to the user's 2090 therapeutic journey. This collaborative care model ensures a holistic approach to the user's 2090 well-being.

The remote interface in an embodiment provides advanced data analytics capabilities, which allow for the processing of large volumes of complex data. It employs machine learning algorithms and statistical tools to identify patterns and trends in the user's 2090 emotional and physiological states. The interface provides visualization tools, such as graphs, heat maps, and timelines, which transform raw data into actionable insights. These visualizations can illustrate the progression of a patient's emotional state over time, the response to specific therapeutic interventions, or the correlation between physiological markers and reported experiences during psychedelic therapy sessions.

Clinicians can use the remote interface to monitor the user's 2090 emotional trends in real-time or review historical data. This is particularly important in the context of psychedelics, where the user's 2090 emotional state can fluctuate significantly. The interface allows clinicians to track these changes and assess the effectiveness of the therapy, including the impact of different dosages, settings, or integration techniques. By having access to a comprehensive user representation, clinicians can tailor their approach to each individual, optimizing the therapeutic process.

The remote interface also serves as a decision support tool, providing clinicians with evidence-based insights that inform patient care. It can integrate with existing therapeutic frameworks and protocols, suggesting interventions or adjustments based on the user's 2090 data. For example, if the system detects a pattern of anxiety or distress in a patient undergoing psychedelic therapy, it can prompt the clinician to consider additional integration support or a modification to the therapeutic setting. The present inventor contemplates embodiments where psychedelics serve as an entry point into the broader therapeutic market, leveraging their efficacy compared to traditional methods. These embodiments are substantiated by pilot clinics where traditional therapists unfamiliar with the use of psychedelics form a significant portion of the clinical staff. As such, embodiments of the system, and particularly those comprising a decision support tool, are designed to support both psychedelic-assisted therapies and non-psychedelic therapies, providing a versatile platform that caters to a diverse range of therapeutic approaches. In certain embodiments, the system is equipped to support traditional therapists in their practice. By providing tools for sentiment analysis, emotional trend monitoring, and personalized generative communications, the system enhances the efficacy of non-psychedelic therapeutic methods. This support is crucial in environments where the use of psychedelics is not feasible or desired, ensuring that all clinicians can benefit from the system's capabilities. Embodiments of the invention provide a comprehensive platform that integrates various therapeutic methods, including those facilitated by psychedelics and traditional therapies. The platform offers a unified approach to emotional well-being, allowing clinicians to select the most appropriate therapy for each individual. This inclusive design ensures that the system can adapt to the evolving landscape of therapeutic practices, whether or not such practices incorporate psychedelic therapies.

In association with various embodiments of the invention, data security and privacy are paramount, especially when dealing with sensitive health information. The remote interface comprises data security and privacy aspects that all data is encrypted and stored in compliance with healthcare regulations, such as HIPAA in the United States. It provides secure access controls, ensuring that only authorized personnel can view or interact with patient data. The storage system is designed to be robust and reliable, with backups and redundancy to prevent data loss. Embodiments of the invention also incorporate aspects responsive to ethical considerations and regulatory compliance, particularly concerning data privacy and the ethical use of psychoactive compounds. These embodiments incorporate advanced security protocols, user consent mechanisms, and compliance with legal standards to ensure the responsible use of the system.

The user representation 3000 within the remote interface in an embodiments comprises a dynamic model that includes both quantitative and qualitative data. It incorporates sentiment and valence analysis derived from the user's 2090 verbal and non-verbal communications, physiological data from sensors, and self-reported measures of well-being. Real-time metrics provide immediate feedback on the user's 2090 state, while historical data allows for the observation of long-term trends and the efficacy of the therapeutic interventions over time.

The type and format of the data communicated between the access module and the remote interface are designed to be interoperable and standardized. For example, audio data may be encoded using advanced audio coding (AAC) for efficient transmission, while physiological data may be formatted according to the Health Level Seven (HL7) or Fast Healthcare Interoperability Resources (FHIR) standards to facilitate integration with electronic health records (EHRs) and other digital health information systems.

The advantages of this system architecture in such contexts are manifold. The real-time data transfer enables dynamic and responsive therapeutic interventions, allowing the system to adapt to the user's 2090 current state and provide immediate support. The multi-modal approach to data collection and communication enables a comprehensive understanding of the user's 2090 emotional and physiological states, leading to more personalized and effective therapy. The secure and standardized communication protocols ensure the privacy and integrity of sensitive health data, which is paramount in the healthcare context. Moreover, the centralized remote interface provides clinicians with powerful tools for monitoring and intervention, potentially leading to improved outcomes and optimizing the use of healthcare resources related to psychedelic therapies.

Various embodiments of the invention comprise a user representation. The user representation 3000 in the context of such embodiments comprises a dynamic, multi-dimensional profile that encapsulates the emotional and physiological state of a client in real-time, as well as historically, throughout their therapeutic journey. This representation is constructed using a variety of data inputs 2020, including but not limited to text, audio, visual cues from facial expressions, symbolic inputs, and direct physiological measures such as heart rate, brain waves from EEG, and other biometric data. These inputs 2020 are captured through the access module's interfaces and processed using multi-modal deep learning methods to quantify and classify the client's emotional expressions and psychological data points. The system maps these data points against established psychological therapeutic frameworks, creating a real-time classification of the client's emotional state. This classification is then used to inform and adapt digital therapy in real-time, providing a closed-loop feedback system that can guide the client towards an optimized emotional state. The user representation 3000 is continuously updated with new data, ensuring that the therapeutic interventions are responsive to the client's evolving needs, particularly in the context of therapies that involve psychoactive compounds, where the client's emotional and cognitive states can be highly variable and sensitive to change.

In an embodiment, the system's architecture is designed to leverage multi-modal deep learning methods, which are executed on a computer processor to analyze and interpret user data. These methods integrate various forms of input, including text, speech, vision, symbols, and brain wave inputs, to determine the user's 2090 emotional expression and valence with high accuracy. The deep learning algorithms are stored on a non-transitory computer-readable medium, which ensures that the learned models and computational instructions are preserved and can be accessed by the processor for real-time data analysis. This medium can include solid-state drives (SSDs), hard disk drives (HDDs), flash memory, or any other form of persistent digital storage that retains data without the need for constant power. Those skilled in the art will appreciated that other non-transitory computer-readable media may be appropriate in the context of embodiments of the invention.

The system's output mechanisms in an embodiment include a display, speaker, and haptic feedback device, which are used to communicate generative communications to the user. Those skilled in the art will appreciated that other output mechanisms may be appropriate in the context of embodiments of the invention. The display, which can be an LCD, LED, OLED screen, or any other visual interface, presents visual content such as text, images, or videos generated by the system in response to the user's 2090 emotional state. The speaker provides auditory output, which can range from simple tones to complex soundscapes or verbal instructions, enhancing the user's 2090 auditory engagement with the therapeutic content. The haptic feedback device offers tactile sensations, such as vibrations or pressure, to provide a physical dimension to the digital therapy, thereby engaging multiple senses for a more immersive therapeutic experience. These output devices are controlled by the system to deliver personalized therapeutic interventions, which are dynamically adjusted based on the real-time analysis of the user's 2090 emotional and cognitive states, as determined by the multi-modal deep learning methods.

Method for Dynamically Monitoring a Client's User Representation 3000 as a Lifelog Embodiments of the invention comprise a method for dynamically monitoring a client's user representation 3000 as a lifelog, which is a comprehensive digital record of the client's emotional and physiological states over time. This lifelog in the context of the preferred embodiment serves as a tool for both the client and clinicians to track the client's well-being and the effectiveness of therapeutic interventions, particularly in the context of treatments involving psychoactive compounds like psychedelics. The concept of a lifelog within the preferred embodiment refers to a dynamic and comprehensive memory archive that is intricately connected to collective semantic spaces, facilitating the identification and tracking of a user's 2090 progression along the psychological continuum of a singular narrative of existences. This lifelog is not merely a repository of events but a structured narrative framework that aligns with the principles of narrative neuroscience and narrative therapy. By continuously capturing and integrating detailed logs of user interactions, emotional states, and cognitive changes, the lifelog maps these elements onto a broader narrative structure, revealing patterns and themes that resonate with the user's 2090 life story. This narrative is constructed in accordance with an embodiment using language processing techniques that detect and interpret the specific patterns of language or "story" used by the user. These patterns indicate the user's 2090 current psychological state and their evolution within the narrative continuum. The lifelog, therefore, plays a role in not only preserving individual experiences but also in contextualizing these experiences within the collective semantic frameworks that define shared human experiences in accordance with the preferred embodiment. By doing so, it provides invaluable insights into the user's 2090 personal growth and their place within a larger existential narrative, supporting targeted therapeutic interventions that are deeply personalized and profoundly resonant with the user's 2090 own life story. This integration of narrative-based data into the lifelog ensures that the system can effectively support the user's 2090 psychological development and well-being through a continuous, narrative-driven engagement.

A step in the method involves receiving session data via the access module. This data is collected from the client's personal digital devices, which may include mobile phones, wearable technology, and specialized medical devices like EEG or fMRI machines. The access module is designed to be compatible with a variety of input methods, ensuring that it can capture a wide range of data types, from audio and visual inputs to biometric and neurological signals. The data is uploaded onto the access module in real-time, providing a continuous stream of information that reflects the client's current state.

The method further comprises the step of processing user data. Once the session data is received, the access module processes this information to derive historical patient response metrics. These metrics are indicative of the client's continuous emotional response to various compounds or natural states. The processing involves algorithms and machine learning models that analyze the data to identify patterns, trends, and anomalies. These computational methods discern structures within the large amount of collected neural data, which are indicative of the patient's cognitive processes and are in an exemplary embodiment stored in long-term memory, such as in an embodiment a computer disk drive or flash memory. By mapping these patterns against known long-term memory functions, the system can detect deviations that may signal disruptions in memory consolidation or retrieval. In such way, embodiments provide for tailoring therapies that aim to strengthen memory retention and recall, thereby supporting the integrity of long-term memory. This step is crucial for transforming raw data into meaningful insights that can inform the client's therapeutic journey.

The method further comprises the step of transferring data to a remote interface. The processed data, along with any unprocessed data, is then transferred from the access module to the remote interface. This transfer allows medical staff to access the information, providing them with a detailed view of the client's historical response metrics over time. The remote interface serves as a centralized platform where clinicians can visualize the data, conduct further analysis, and make informed decisions about the client's care. The interface is designed to present the information in an intuitive and accessible manner, with tools for data visualization and trend analysis.

The method further comprises the step of enabling lifelog enrichment. In association with the preferred embodiment, the lifelog is enriched with context-related metadata, which includes the user data and any generative content provided by the system. This metadata provides cues for recall and reflection on the information held in the digital memory. The process of monitoring, analysis, and adaptation is enhanced by this enrichment, as it allows for a more nuanced understanding of the client's experiences and responses to therapy. The lifelog becomes a powerful tool for tracking the client's progress and for clinicians to tailor therapeutic interventions to the client's specific needs.

The method in an embodiment further comprises actively informing digital therapy. The lifelog in the preferred embodiment is not just a passive record; it actively informs adaptive digital therapy. Based on the historical data and real-time metrics, in an embodiment the method further comprises the step of adjusting the generative communications sent to the client. In the context of the system, adjustments are made in response to the client's current state, with the goal of providing optimal therapeutic support. For example, if the lifelog indicates that the client is experiencing increased stress or anxiety, the system may modify the generative content to include calming audio or visual stimuli. The steps associated with the method aspects of the invention contribute to the creation of a detailed and actionable digital record that supports the client's therapeutic process, particularly in the context of treatments involving psychoactive compounds. Thus, the lifelog associated with the preferred embodiment serves as a critical tool for ensuring that therapy is responsive, personalized, and effective over the long term.

Additional relevant steps comprise enriching lifelogs with context-related metadata. In association with embodiments of the invention, such steps provide enhancements to the therapeutic process. By incorporating context-related metadata into these lifelogs, the system provides a rich tapestry of information that aids in the recall and reflection of past experiences.

A step associated with the enrichment of lifelogs comprises appending metadata to each entry in the lifelog. This metadata can include timestamps, location data, physiological metrics, the type of generative content presented, user interactions, and any compounds or medications the user 2090 may have been using at the time. The inclusion of such detailed metadata allows for a nuanced understanding of the circumstances surrounding each logged event, providing insights into the factors that may influence the user's 2090 emotional state.

For instance, if a user 2090 reports feeling particularly anxious, the metadata may reveal that this emotional state correlates with specific environmental factors, such as being in a crowded space, or it may be temporally linked to the ingestion of a particular compound. This information is crucial for both the user 2090 and the clinicians to understand the triggers and patterns of the user's 2090 emotional responses.

The lifelog serves as a digital memory that the user 2090 and their healthcare providers can access for monitoring and analysis. The process of reviewing the lifelog includes the step of identifying trends, the effectiveness of interventions, and the progress towards therapeutic goals. The associated method also may optionally comprise providing a platform for the user 2090 to reflect on their experiences, which is an essential component of the integration process in psychedelic therapy.

Moreover, in an embodiment the aspect of the invention comprising the adaptive digital therapy system utilizes the enriched lifelogs to enhance human-computer interaction. The system can incorporate the step of analyzing the metadata to personalize the generative content, making it more relevant and effective for the user. For example, if the system recognizes that a user 2090 responds positively to certain types of audiovisual stimuli under specific conditions, it can adapt the content to include these elements when similar conditions are detected in the future.

The inclusion of context-related metadata in lifelogs also supports integrated methods of harm reduction. By understanding the context of each user's 2090 experiences, the system can enable the step of proactively adjusting therapeutic protocols to mitigate risks. For example, if the metadata indicates that a user 2090 is likely to experience heightened anxiety after consuming a particular psychoactive compound, the system can prepare content designed to soothe and reassure the user 2090 in anticipation of this response.

The enrichment of lifelogs with context-related metadata is an aspect of the adaptive digital therapy system in an embodiment of the invention, providing a foundation for personalized care, deeper self-understanding, and effective harm reduction strategies. An associated benefit of the embodiment is that it enables a dynamic and responsive therapeutic experience that is tailored to the unique journey of each user.

The preferred embodiment of the invention in some aspects builds upon methods and systems for monitoring psychoactive therapy sessions. An example of such methods and systems are described within United States Patent Application Publication 2023/0162851, published on May 25, 2023, which is hereby incorporated by reference in its entirety. This example focuses on the clinical safety of psychoactive therapies through remote monitoring and patient response metrics, the present invention expands upon these features by integrating advanced machine learning models and multi-modal data analysis. Such integration allows for a more nuanced understanding of the patient's emotional and cognitive states, enabling the system to provide real-time, adaptive digital therapy that is personalized to the patient's evolving needs. The present preferred embodiment of the invention expands upon such concepts by providing enriching lifelogs with context-related metadata, which allows for a deeper layer of data for monitoring and analysis, contributing to a more comprehensive user representation 3000 that informs therapeutic adjustments.

Furthermore, the present preferred embodiment builds upon the example present within United States Patent Application Publication 2023/0162851 by incorporating novel methods of communication, such as the use of symbolic language input methods, to articulate complex experiences during extended state sessions. This approach addresses the limitations of traditional verbal communication in expressing the profound effects of psychoactive compounds, thereby enhancing the patient's ability to convey their experiences for therapeutic integration. Additionally, the present preferred embodiment extends the application of the system to include natural emotional states, allowing for the derivation of user representations without the influence of ingested compounds, thus broadening the scope of the system's utility beyond psychoactive therapy sessions.

Method for Dynamically Monitoring a Client's User Representation

Embodiments of the invention further comprise a method for dynamically monitoring a client's user representation 3000 to identify potentially adverse emotional states. In an embodiment, the method can be performed in association with the following steps in concert with the other aspects of the invention as disclosed herein:

Receiving user data via an access module, wherein the receiving includes uploading session data onto the access module from the client's personal digital devices, which may include mobile devices, wearable technology, or computers.

Processing the received user data within the access module to derive historical patient response metrics, wherein the processing step involves analyzing the user data to quantify the patient's continuous emotional response to various compounds or natural states, and wherein the processing includes the use of a processor within the access module.

Transferring the derived patient response metrics from the access module to a remote interface, wherein the transferring step includes communicating the patient's historical response metrics over time to medical staff via the remote interface, and may also include transferring unprocessed data from the access module to the remote interface for further analysis.

Training a model to measure the state of the user, wherein the training includes using machine learning algorithms to analyze the user data and generate a user representation 3000 that reflects the user's 2090 emotional state.

Calculating a score of the user 2090 based on the user representation, wherein the calculating step involves determining a valence score that quantifies the user's 2090 emotional state, and wherein the score is compared to a predetermined threshold to assess the presence of potentially adverse emotional states.

Modifying adaptive communications in response to the score being lower than the threshold, wherein the modifying step includes adjusting the content, format, or delivery of therapeutic communications to address the identified adverse emotional states, and may involve personalizing the therapeutic interventions based on the user's 2090 specific needs.

Notifying medical staff of a potential crisis when the score is indicative of an adverse emotional state, wherein the notifying step includes sending alerts or detailed reports to medical staff via the remote interface, enabling timely intervention and support for the patient.

These steps provide a structured approach to monitoring and responding to a client's emotional well-being, leveraging other aspects of embodiments of the invention to offer personalized and adaptive support. The integration of these steps into a cohesive system allows for the real-time identification and management of adverse emotional states, potentially improving therapeutic outcomes and patient care.

Method of Creating an Encoded Map of Language Patterns

It is an aspect a preferred embodiment to provide a method of creating an encoded map of language patterns. In association with this method, digitally recorded data, specifically evoked potential readings, are analyzed to create an encoded map of the user's 2090 language patterns within the brain. This method represents an approach in association with the preferred embodiment of understanding and interpreting the neural basis of language and communication, particularly in the context of therapeutic settings where understanding nuanced patient responses is crucial. Embodiments of the method comprise the following steps:

A step of the method comprises digitally recording evoked potentials. This step involves the use of non-invasive neuroimaging technologies, such as electroencephalography (EEG), to digitally record evoked potentials. Evoked potentials are brain responses that are elicited by sensory, cognitive, or motor events. For instance, when a user 2090 is presented with a stimulus such as a word, sound, or image, the brain generates an electrical response that can be captured by EEG electrodes placed on the scalp. The quality of these recordings is paramount, and thus, the system must ensure high-resolution data capture, possibly employing advanced EEG systems with multiple channels and high sampling rates to accurately detect the subtle changes in brain activity that correspond to different evoked potentials.

Another step of the method comprises encoding evoked potentials as words. Once the evoked potentials are recorded, the next step is to encode these readings into a format that represents individual words or language elements. This encoding process involves the translation of the complex waveforms obtained from the EEG into a digital code that corresponds to specific words in the user's 2090 language. Advanced signal processing algorithms are used to analyze the characteristics of the evoked potentials, such as amplitude, latency, and frequency components, to determine their association with particular language constructs. Machine learning models, trained on large datasets of brain activity correlated with known language patterns, are employed to facilitate this encoding process, ensuring that the system can accurately map the neural responses to the correct linguistic elements.

Another step of the method comprises logging in a neural library. In association with such step, the encoded words are logged in a neural library, which serves as a database of the user's 2090 language patterns as represented by their brain activity. In association with an embodiment, the neural library is a dynamic repository that is continually updated with new data, allowing for the refinement of the language map over time. The library stores not only the encoded words but also the context in which they were generated, such as the emotional state of the user 2090 or the specific compounds affecting their cognitive processes at the time of data capture. This contextual information is crucial for interpreting the language patterns in relation to the user's 2090 experiences and emotional responses.

Another step of the method comprises developing an encoded map of language patterns. An intended result associated with preferred uses of method is the development of an encoded map of the user's 2090 language patterns within the brain. This map provides a visual or computational representation of the relationship between specific evoked potentials and the words or language elements they correspond to. The map can be used to predict how the user 2090 might respond to different stimuli or to understand the underlying neural mechanisms of their language processing. In therapeutic settings, this map provides clinicians with a deeper understanding of the patient's communicative abilities and challenges, particularly in cases where traditional communication is impaired.

In a therapeutic context, advantages of the method include enhanced communication with patients who may have difficulty expressing themselves due to various conditions. By understanding the patient's unique neural language map, therapists can tailor their communication strategies to align with the patient's cognitive and emotional processing capabilities. This personalized approach can lead to more effective therapy sessions, as patients are better understood and can engage more meaningfully in the therapeutic process.

In one embodiment of the invention, the digitally recorded data, which captures the neural responses of the brain, is transferred from the access module to a neural library. This transfer forms a step in creating a bridge between the raw EEG data and its meaningful interpretation as language. The neural library serves as a comprehensive database that stores digital representations of neural responses, effectively creating a lexicon of brain activity associated with specific words or language constructs. This process involves the conversion of complex neural patterns into a format that can be recognized and utilized by machine learning models. The data is formatted as continuous thought to language transcriptions, which are sequences of digital data that represent the electrical activity of the brain as it responds to or generates language. These transcriptions are not static; they are continually updated and refined as new data is collected, allowing the system to adapt to the individual's unique neural language patterns over time.

To decode the neural signals into a continuous stream of understandable language, machine learning models are employed within the system in accordance with the preferred embodiment. These models are trained on extensive datasets that include a wide range of neural responses paired with the corresponding linguistic output. The training process involves exposing the model to various neural patterns and the words or phrases they represent, allowing the model to learn the associations between specific brain activities and language elements. Once trained, the model can take new, unseen neural data and predict the associated language output with a high degree of accuracy. This capability is particularly advantageous for real-time applications, such as neurofeedback in therapeutic settings or communication aids for individuals with speech impairments. By providing a continuous stream of language that reflects the user's 2090 thought patterns, the system can facilitate more natural and intuitive communication, even in the absence of traditional speech or motor functions.

To further enhance the system's capabilities in accordance with an embodiment, the machine learning models are integrated into a dynamic, cooperative coevolutionary framework characterized as a guided self-organizing cognitive architecture with cooperative coevolution dynamics, that includes both hierarchical and user-specific adaptive models. This framework is designed to optimize cognitive states, maintain homeostasis, and dynamically adjust to the user's 2090 interactions, employing the following components in accordance with embodiments:

Hierarchical Multimodal Self-Organizing Map (HSOM): Executed on a computer processor, the HSOM processes and analyzes inputs 2020 including text, speech, vision, symbols, and brain wave data. It establishes a reference state in a hierarchical structure that processes sensory-motor and symbolic information, mimicking complex neural processing structures similar to those in the human brain. This model represents optimal cognitive states and coherent brain state models, serving as a top-down guide for the system.

Dynamic User-Specific Models (GHSORMs): Growing Hierarchical Self-Organizing Representation Maps are tailored for each user 2090 to dynamically represent their current cognitive and emotional states. These models adjust based on user interactions, evolving under the guidance provided by the hierarchical structure of the HSOM. They incorporate the physiological perspective of a regulated nervous system, aiming to maintain homeostasis.

Homeostasis Management Module: This module, executed on the computer processor, leverages data from both the HSOM and the user-specific GHSORMs to model the user's 2090 physiological and psychological needs. It generates personalized behavioral interventions aimed at maintaining or guiding the user's 2090 emotional and cognitive states within a predefined homeostatic range specified by the HSOM.

Meta-Learning Optimization: Implemented within the computer processor, meta-learning models optimize the learning process of both the HSOM and the GHSORMs. They dynamically adjust hyperparameters based on the user's 2090 ongoing interactions with the system, thereby enhancing the integration of therapeutic experiences across various interactions.

Real-Time Dynamic User Representation: The system continually updates a dynamic user representation 3000 that includes a multi-modal feedback profile, adapting to the user's 2090 preferred communication modes. This profile adjusts in real-time in response to the user's 2090 interaction with the system's outputs.

Integrated Multi-Sensory Output System: The system outputs generative communications through an integrated output system that includes a display for visual content, speakers for auditory content, and a haptic feedback device for tactile content. Controlled by the computer processor, this system delivers a multi-sensory experience that is responsive to the dynamic user representation 3000 and aims to guide the user 2090 towards the predefined homeostatic range.

This guided framework, self-organizing cognitive architecture with cooperative coevolution dynamics, utilizes the valence score as the game theoretic mechanism to dynamically adjust the generated content, ensuring that the therapeutic interventions are precisely tailored to the user's 2090 evolving needs and states.

In certain embodiments of the invention, the digitally recorded data encompasses a broader spectrum of cognitive activity by capturing neural responses associated with multiple semantic representations. This data is transferred from the access module to a neural library, where it is cataloged as part of a continuous thought to language transcription process. The neural library, in this context, functions as an database that not only stores individual words but also complex phrases, idiomatic expressions, and even nonverbal communicative elements that are represented by distinct neural patterns. The digital representations of these neural responses are encoded to reflect the intricate web of language patterns that exist within the user's 2090 brain. This encoding captures the nuances of language, including context, tone, and emotional content, which are essential for conveying the full meaning behind a user's 2090 thoughts. As the system, in accordance with its associated methods of use, encounters new variations of neural responses, it updates the neural library, thereby refining the encoded map and enhancing the system's ability to interpret and translate brain activity into rich, multi-faceted language.

An associated step of mapping language inputs from the user 2090 to a neural library may thus take place. In accordance with such step in an embodiment, language inputs from the user, encompassing spoken or written words, are mapped to a neural library, which is characterizable as a comprehensive database that stores neural patterns associated with specific linguistic elements and their corresponding sentiment scores. This mapping process in an embodiment involves sentiment analysis and emotional expression algorithms that calculate a valence score for each input. The valence score quantitatively represents the emotional content of the language input, ranging from negative to positive emotional states. Each language input, along with its associated valence score, is recorded in the user's 2090 life log as part of a gradated representation of the user's 2090 emotional and cognitive experiences over time. This life log in an embodiment serves as a dynamic record, continuously updated with new inputs and scores, creating a detailed knowledge graph of the user's 2090 interactions and emotional states. The recorded scores in the life log in accordance with an embodiment are systematically compared against optimal patterns and semantic spaces defined in the Hierarchical Multimodal Self-Organizing Map (HSOM). This comparison involves calculating a delta, which represents the deviation of the user's 2090 current emotional and linguistic state from the optimal states determined in accordance with an embodiment and stored in the HSOM. By identifying this delta, the system can accurately determine the necessary adjustments or interventions needed to guide the user 2090 towards a more balanced or desired state. Based on the derived delta, the system dynamically adjusts the generative communications delivered to the user. These adjustments are tailored to address the specific needs identified through the comparison, ensuring that each piece of content delivered-whether text, audio, or visual-effectively contributes to moving the user's 2090 current state towards the optimal state as defined by the HSOM. This process not only enhances the personalization of the therapy associated with embodiments but also ensures that the interventions are grounded in a deep understanding of the user's 2090 evolving emotional landscape.

The process of developing an encoded map of the user's 2090 language patterns within the brain involves computational techniques and machine learning algorithms that can handle the complexity of multiple semantic representations. These algorithms analyze the digital representations of neural responses for patterns that correlate with specific semantic meanings. Over time, as the system processes more data, it becomes increasingly adept at recognizing and predicting the user's 2090 language patterns, effectively creating a personalized neural language map. This map comprises not only a static record but a dynamic model that evolves with the user's 2090 experiences and changes in cognitive or emotional states. It allows for real-time interpretation of the user's 2090 thoughts and intentions, which can be particularly beneficial in therapeutic settings where understanding the patient's internal dialogue is crucial. For example, in the context of mental health treatment, the ability to accurately translate a patient's thoughts into language can provide invaluable insights into their mental state, aiding in diagnosis and the tailoring of treatment plans. This level of understanding can also empower patients, giving them a voice when traditional means of communication may be compromised or inadequate.

An aspect of the preferred embodiment of the invention is the valence score. In the context of the preferred embodiment, the machine learning model plays a crucial role in assessing and responding to a user's 2090 emotional state through the calculation of a valence score. The valence score is not a simple binary measure but is quantified on a continuum that reflects the degree of pleasure or displeasure an experience elicits, ranging from highly negative to highly positive. This nuanced approach allows the valence score to capture subtle differences in emotional experiences, such as distinguishing between feeling content (mildly positive) and elated (strongly positive), or between being annoyed (mildly negative) and furious (strongly negative).

The valence score is derived from the analysis of the encoded semantic representation of the user's 2090 neural responses, capturing the complex interplay between cognitive content and emotional nuances. The model evaluates various aspects of the neural data, such as the presence of specific brainwave patterns that have been associated with different emotions in psychological research, and the intensity and variability of these patterns, which can indicate the strength and stability of the emotional state. In affective science, emotions are often mapped on a two-dimensional space involving both valence and arousal (how energizing or enervating an emotion is), providing a comprehensive framework for understanding and responding to the user's 2090 emotional dynamics within the system.

Once the valence score is determined, it serves as a benchmark for mapping the user's 2090 current emotional state against existing therapeutic frameworks. This mapping is crucial for identifying the most suitable therapeutic interventions based on the user's 2090 specific emotional needs. For instance, a low valence score, indicating a negative emotional state, might prompt the system to initiate interventions aimed at mood elevation or anxiety reduction.

The system then generates digitally transmitted data as tailored interventions designed to modulate the user's 2090 emotional state in a direction that aligns with therapeutic goals. These interventions are adaptive, meaning they are responsive to the real-time valence score of the user, and can be delivered in various formats in association with exemplary embodiments.

In some embodiments of the invention, the digitally transmitted data includes the use of Visible Light Communications (VLC), which is a method of data transmission that utilizes light visible to the human eye. One of the techniques employed within VLC is Pulse Code Modulation (PCM), which encodes the data into pulses of light at varying intensities and durations. This method is particularly advantageous in therapeutic settings where traditional radio-based communication might interfere with sensitive medical equipment or where privacy is a concern, as the light does not penetrate through opaque structures like walls. VLC can be integrated into the ambient lighting of a room or into wearable devices, providing a seamless and unobtrusive way to deliver therapeutic content. For example, the lighting in a patient's room could be modulated to deliver therapeutic messages or to create an environment conducive to relaxation or focus, depending on the patient's current emotional valence score.

Optogenetic neural modulation represents another exemplary application of light in the context of embodiments of the invention. This technique involves the use of light to control neurons that have been genetically modified to express light-sensitive ion channels. By delivering precise patterns of light to these neurons, it is possible to modulate specific neural circuits and influence the patient's emotional state. This form of therapy could be particularly effective when combined with the real-time emotional valence scoring system described in the invention. The system could, for instance, trigger an optogenetic device to deliver a specific light pattern designed to elevate the valence score of a patient experiencing negative emotions. The integration of optogenetic neural modulation with the invention's machine learning model and valence scoring system creates a powerful platform for personalized and responsive therapy that can adapt to the changing emotional needs of the patient.

The incorporation of the valence score into the system's therapeutic approach allows for a highly personalized and scientifically grounded method of treatment. By continuously monitoring and responding to the user's 2090 emotional valence, the system can provide interventions that are both timely and relevant to the user's 2090 current emotional needs. This approach to therapy, rooted in the quantifiable assessment of emotional states, represents a significant advancement in the field of mental health treatment and emotional well-being support.

In association with certain embodiments of the invention, the access module is equipped with enhanced interactive capabilities that allow for the direct self-reporting of adverse emotional states by the user. This feature is critical for instances where the user 2090 is experiencing distress or other negative emotional states that require immediate attention from medical staff. The access module includes a user interface element, such as an emergency button or a panic switch, which the user 2090 can activate to initiate a rapid response protocol.

Upon activation of the user interface element, the access module generates and transmits a remote signal to a remote interface. This signal is encoded with information that indicates the user's 2090 need for urgent care. The remote interface, which is monitored by medical staff, receives the signal and decodes it to understand the nature of the emergency. The system is configured to prioritize these signals, ensuring that they are immediately brought to the attention of the medical team.

The access module's user interface is designed to be intuitive and easily accessible, even under duress. It may include visual cues, haptic feedback, or auditory signals to confirm to the user 2090 that their distress signal has been successfully sent. Additionally, the access module may provide the user 2090 with immediate feedback or instructions on what to do while waiting for assistance. This could include automated messages that guide the user 2090 through calming techniques or provide reassurance that help is on the way.

In some embodiments, the access module may also automatically collect and transmit additional data relevant to the user's 2090 current state when the emergency signal is activated. This data could include the user's 2090 location, recent biometric readings, a log of recent user interactions with the system, or any other information that could assist medical staff in assessing the situation and providing appropriate care.

The remote interface, upon receiving the distress signal, may also trigger additional protocols within the healthcare system. This could include alerting on-call mental health professionals, mobilizing emergency response teams, or preparing a treatment room for the user's 2090 arrival. The system ensures that all relevant patient information is readily available to the medical staff, allowing them to act swiftly and effectively.

This direct interaction mechanism within the access module serves as a critical safety feature of the invention, providing users with a lifeline during moments of crisis. It underscores the system's commitment to user safety and the provision of immediate support, enhancing the overall efficacy of the therapeutic interventions.

Method of Labeling User Inputs

The method of labeling user inputs 2020 as affected by various compounds or natural states provides a nuanced approach to monitoring the influence of different substances or physiological conditions on a user's 2090 emotional and cognitive states. This method is particularly useful in therapeutic settings where understanding the impact of medications, such as Selective Serotonin Reuptake Inhibitors (SSRIs), 5-HT2A agonists like LSD and psilocybin, dissociatives, empathogens, or even the user's 2090 natural state, is crucial for personalized treatment.

The method begins with the receiving of user data via an access module. This step involves the user 2090 uploading data related to their emotional, cognitive, or physiological state onto the access module. The data can be collected through various means, such as self-reported mood assessments, biometric sensors, or direct input from the user 2090 through a digital interface on their personal devices, which may include smartphones, wearable technology, or computers.

Once the data is received, the next step involves returning the user data to the user's 2090 personal digital devices for display. This step is facilitated by a processor within the access module, which processes the received data and ensures that it is formatted and transmitted back to the user's 2090 device in a user-friendly manner. The display of this data allows the user 2090 to review and reflect on their current state and the potential effects of any substances they have ingested or their natural physiological condition.

The method includes an enabling step, where a labeling method is provided on the input entry interface. This labeling method allows users to tag or label their inputs 2020 with information about any compounds they have taken or their natural state at the time of data entry. The labels can be pre-defined within the system or entered manually by the user, offering flexibility and precision in capturing the context of their emotional and cognitive states.

Following the labeling, the method involves logging the user label via the access module. The processor within the access module records the labeled data, creating a log that associates specific emotional or cognitive states with the corresponding compounds or natural states. This log serves as a valuable data set for tracking the user's 2090 responses over time and understanding the individualized effects of various substances or conditions.

In some embodiments, the method further includes transferring the patient self-report label from the access module to a remote interface. This transfer step involves communicating the labeled data to a centralized system accessible by medical staff. The remote interface updates the user representation 3000 with the new labeled data, providing healthcare professionals with a comprehensive view of the correlation between compound usage or natural states and the patient's emotional response. This information is critical for clinicians to tailor treatment plans, adjust medication dosages, or provide targeted therapeutic interventions based on the user's 2090 unique experiences and reactions.

By incorporating these steps, the method offers a systematic approach to capturing and utilizing self-reported data in a therapeutic context, enhancing the ability of healthcare providers to deliver personalized care and support to users based on their individual responses to various compounds or natural states Method of Providing Established Therapeutic Protocols as Digital Therapies The method of providing established therapeutic protocols as digital therapy encompasses an approach to delivering personalized treatment through various digital media, such as text, audio, video, and symbols. This method is particularly relevant in the context of psychedelic harm reduction, where the goal is to mitigate the risks associated with psychedelic experiences and to facilitate positive outcomes for long-term well-being. Embodiments of the method may comprise the following steps:

The method begins with the step of receiving of user data at an access module. This data can be in the form of live-streamed text, audio, or video captured during the user's 2090 interaction with generative content, which is content that is dynamically generated in response to the user's 2090 input or state. The access module serves as the interface for collecting this data, which may include the user's 2090 verbal feedback, physiological responses, or interactions with a digital platform.

Once the user data is received, the method involves executing a machine learning model to determine an indication of the user's 2090 state associated with the digital therapy. The machine learning model analyzes the user data to assess the user's 2090 engagement with the therapy, their emotional and cognitive responses, and their progression towards therapeutic goals. The indication of state is a metric that reflects the user's 2090 current position within the therapeutic process and their movement towards an optimal mental state.

Based on the indication of state, the method includes determining a modification to the digital therapy. This step involves adjusting the generative content or therapeutic interventions to better align with the user's 2090 needs. For example, if the user's 2090 indication of state suggests heightened anxiety, the digital therapy may be modified to include calming audiovisual elements or guided relaxation exercises. In some embodiments, the system utilizes real-time biofeedback based on physiological data to offer immediate therapeutic interventions. For instance, the system may initiate stress-reduction protocols automatically in response to detected physiological indicators of stress or anxiety.

Furthermore, the method comprises the step of indicating of state to monitor and adjust the generative content. This involves a continuous feedback loop where the machine learning model refines the generative content in real-time, ensuring that the digital therapy remains responsive to the user's 2090 evolving state. Adjustments to the content can include changes in the narrative, pacing, sensory input, or interactive elements of the digital therapy.

In the specific context of psychedelic therapy, the method includes generating protocols for pre-session preparation and post-session care. Pre-session protocols may involve preparing the user 2090 for the experience by setting intentions, providing educational content, or guiding them through relaxation techniques. Adaptive digital therapy during the acute phase of treatment is tailored to the user's 2090 real-time responses, with the machine learning model making adjustments to the therapy based on the user's 2090 indication of state.

In association with the context of the preferred embodiment of the invention, the 72-hour post-treatment window associated with the relevant therapies is a period of heightened neuroplasticity and vulnerability. During this time, the method continues to provide digital therapy that supports the user's 2090 integration process. This may include reflective exercises, mood tracking, and the provision of supportive content that reinforces the therapeutic insights gained during the psychedelic experience.

Aspects of the invention are directed to an improved identification of neuroplastic windows. Embodiments facilitate the labeling of psychoactive compounds and their administration dates as part of the therapeutic monitoring process. This manual labeling serves as an initial method for identifying neuroplastic windows-critical periods following compound administration when the brain's capacity for change and reorganization is heightened. In association with embodiments, the system is designed to evolve from manual labeling to automated detection of neuroplastic windows through continuous monitoring and data analysis. In embodiments, the system employs continuous monitoring of the user's 2090 physiological and psychological states through a combination of biometric sensors, self-reporting tools, and neural imaging techniques. The collected data is analyzed to detect patterns indicative of increased neuroplasticity, such as changes in brainwave activity, heart rate variability, and other biomarkers associated with the brain's heightened ability to reorganize and form new connections. Embodiments of the invention integrate multimodal data to provide a comprehensive assessment of the user's 2090 neuroplastic state. This includes not only physiological and neural data but also behavioral and cognitive metrics that may signal the user's 2090 readiness for therapeutic interventions aimed at cognitive and emotional development. By leveraging machine learning algorithms and pattern recognition, including the machine learning algorithms described herein, the system analyzes physiological and psychological data to predict when a user 2090 is entering a state of heightened neuroplasticity, in an embodiment represented by a graph as depicted by FIG. 9. The system utilizes machine learning algorithms that are trained on datasets comprising various biomarkers collected during and after the administration of psychoactive compounds. These algorithms are designed to recognize the onset of neuroplastic windows by identifying characteristic data signatures that correlate with the brain's plastic state. The system in an embodiment incorporates a feedback loop where the effectiveness of interventions during identified neuroplastic windows is used to refine the machine learning models. This iterative process enhances the system's ability to accurately detect future windows and tailor interventions accordingly. Once a neuroplastic window is identified, the system in an embodiment facilitates the delivery of personalized therapeutic content and interventions. This may include guided imagery, cognitive-behavioral exercises, or other forms of psychotherapy that are optimized for efficacy during periods of heightened neuroplasticity.

The significance of neuroplastic windows, also referred to as integration windows or critical reward periods, is relevant to embodiments of the invention in the context of the therapeutic journey. These periods are characterized by the brain's enhanced ability to reorganize and form new neural connections is at its peak. It is within these windows that the system provides crucial support to users, assisting them in processing their experiences and rewriting their cognitive schemas and narratives. By recognizing the biochemical underpinnings of neuroplasticity, such as the role of neurotransmitters like BDNF (Brain-Derived Neurotrophic Factor) in synaptic growth, the system can optimize intervention strategies to coincide with natural peaks in neuroplastic potential. This ensures that therapeutic activities, whether they be cognitive exercises or guided meditations, are delivered when the brain is most biochemically primed for change. In an exemplary embodiment, the system comprises a suite of technologies to support users during these critical reward periods. This includes non-invasive neuroimaging techniques like MEG to capture brain activity with high temporal resolution, AI-driven analysis to decode this activity into meaningful representations, and real-time feedback mechanisms to guide the therapeutic process. The system's ability to visualize the user's 2090 internal experience provides a unique avenue for users to engage with and understand their subconscious thoughts and emotions, facilitating a more profound integration process. By continuously monitoring a range of biomarkers, including neurochemical signals, the system can identify the onset of neuroplastic windows with greater precision. This allows for the timely delivery of personalized therapeutic interventions that are synchronized with the user's 2090 individual neurochemical profile. It is further an aspect of the system to leverage data analytics to guide users in reconstructing their cognitive schemas. By analyzing patterns in the user's 2090 responses and brain activity, the system identifies key themes and narratives that emerge during the integration phase. Therapeutic content is then tailored to these themes, providing users with insights and cognitive tools to reshape their narratives in a way that aligns with their therapeutic goals.

Within the context of embodiments of the invention, cognitive schemas are understood as the mental frameworks that shape an individual's perception of the world, influencing thoughts, emotions, and behaviors. These schemas are formed through life experiences and can sometimes become maladaptive, contributing to negative patterns that affect mental health. The system described herein is designed to identify and target these maladaptive schemas during neuroplastic windows, employing a combination of real-time neural monitoring, data analysis, and personalized therapeutic content to facilitate their reconfiguration.

The preferred embodiment's multi-modal approach enables the precise detection of when a user's 2090 brain is most receptive to forming new connections and reorganizing existing ones. During these periods, the system delivers interventions tailored to the user's 2090 unique psychological profile, which may include guided cognitive exercises, exposure to new perspectives, and the reinforcement of positive narratives. By doing so, the system helps users to reshape their cognitive schemas, replacing outdated or harmful beliefs with healthier, more adaptive ones.

The therapeutic reconfiguration of cognitive schemas is supported by the system's ability to process and interpret complex neural data. Machine learning algorithms associated with the system analyze patterns in brain activity that correlate with entrenched thought processes and emotional responses. This analysis informs the generation of therapeutic content that is designed to challenge and ultimately transform these ingrained schemas.

In association with an exemplary use, a user 2090 might engage with the system by reflecting on visual or auditory content that symbolizes aspects of their cognitive schema. As the user 2090 interacts with this content, the system measures their neural and physiological responses, adjusting the therapeutic approach in real-time to encourage schema evolution. This dynamic process not only supports the user 2090 in developing a more nuanced understanding of their mental patterns but also empowers them to actively participate in the reshaping of their cognitive landscape.

A method associated with an embodiment of the invention offers a structured and adaptive framework for delivering digital therapy that is attuned to the user's 2090 individual journey through psychedelic treatment. This approach enhances the potential for positive outcomes and supports the user's 2090 path towards long-term well-being.

Certain embodiments of the invention incorporate virtual and augmented reality (VR/AR) technologies to create immersive therapeutic environments. These environments are dynamically modulated based on the user's 2090 emotional feedback, providing a supportive setting that complements the therapeutic process. Aspects of the preferred embodiment of the invention builds upon previously known concepts associated with adaptive digital therapy contexts. Examples of such contexts are described within U.S. Pat. No. 11,660,419, issued on May 30, 2023, which is hereby incorporated by reference in its entirety. Embodiments of the present invention build upon the concepts disclosed within the '419 patent by introducing improvements upon frameworks for adaptive digital therapy that not only generate and manipulate multi-sensory environments but also incorporate a user's 2090 real-time physiological and cognitive data. While the invention disclosed in the '419 patent provides an example of creating immersive therapeutic experiences using VR and sensory presentation devices in conjunction with drug treatments, embodiments of the present invention expand upon this by utilizing a comprehensive set of user data, including but not limited to EEG and PPG sensor data, to dynamically adjust the therapeutic environment. This advancement ensures that the digital therapy is continuously adapted to the user's 2090 current state, thereby providing a highly personalized therapeutic experience that can evolve with the user's 2090 changing needs.

Moreover, the present preferred embodiment differentiates itself from '419 patent by employing a novel symbolic language input method that allows users to communicate their experiences during therapy sessions more expressively. This aspect is particularly beneficial in sessions where users may encounter non-ordinary states of consciousness, such as those induced by psychedelics, where traditional language may be insufficient to describe their experiences. The preferred embodiment also is associated with the capability to cater to users in natural emotional states, thereby broadening the applicability of the system beyond the scope of drug-induced therapy sessions. In accordance with various aspects of the invention, the term language—particularly as associated with language outputs—has a broadened definition. In this context, language may refer not only to the typically understood meaning of language, i.e as a method of human communication, consisting of words used in a structured and conventional way and conveyed by speech, writing or gesture, but also refers to the conveyance of information in general by non-traditionally understood means, such as via bits, qubits, language, electricity, electric signals, light, sound, and even changes in physiological characteristics such as blood flow. It is an aspect of various embodiments to translate any signals that otherwise may not traditionally be understood as language into meaningful information as inputs or outputs in association with the invention described herein.

In the context of aspects of embodiments and methods of the invention relating to adaptive digital therapy, the derivation of a user representation 3000 that accurately reflects the user's 2090 emotional and cognitive states is provided. This representation is relevant for tailoring the therapeutic experience to the individual's needs. The methods described herein enable the creation of such a user representation, which can be derived regardless of whether the user 2090 has ingested psychoactive compounds or is in a natural state.

In various aspects associated with embodiments of the invention, the derivation of a user representation 3000 includes several key components related to data collection, data processing, feature extraction, a user representation 3000 module and the associated contextual analysis.

The access module collects a wide array of data from the user, which may include self-reported mood assessments, physiological data from wearable sensors (such as heart rate, skin conductance, and body temperature), and behavioral data (such as sleep patterns and activity levels). This data is collected continuously or at specified intervals, providing a rich dataset that reflects the user's 2090 natural emotional states over time.

Advanced algorithms within the access module process the collected data to identify patterns and trends. These algorithms may include machine learning techniques that can discern subtle changes in the user's 2090 emotional state, even in the absence of psychoactive compounds. The processing includes normalization of data to account for individual baselines and variability.

From the processed data, specific features are extracted that are indicative of the user's 2090 emotional and cognitive states. These features could include metrics such as the variability in heart rate, changes in sleep quality, or frequency of certain mood descriptors used in self-reports.

The extracted features are used to build a dynamic user representation 3000 model. This model is a digital profile that encapsulates the user's 2090 emotional and cognitive states and is updated in real-time or near-real-time as new data is collected. The model can also incorporate historical data to provide context and enhance the accuracy of the representation.

The user representation 3000 model includes contextual analysis to understand the circumstances surrounding the user's 2090 emotional states. This analysis considers factors such as time of day, recent activities, and environmental conditions that could influence the user's 2090 mood and cognitive function.

Based on the user representation 3000 model, the adaptive digital therapy system can make adjustments to the therapeutic content and interventions. For example, if the model indicates that the user 2090 is experiencing increased stress, the system may suggest stress-reduction techniques or modify the therapeutic content to address this state.

A feedback loop is established where the user's 2090 interactions with the therapeutic system are used to refine the user representation 3000 model further. The system learns from each interaction, enhancing its ability to predict and respond to the user's 2090 emotional states.

The user representation 3000 model can be integrated and/or embedded with clinical practice, as depicted in FIG. 10 in an exemplary embodiment as 2080, providing healthcare professionals with a tool to monitor the user's 2090 emotional well-being and make informed decisions about their care. In association with embodiments, clinicians can access the model to view trends, receive alerts, and collaborate with the user 2090 on treatment plans, including via integrations with an EHR in an embodiment.

By incorporating these components, the methods and other aspects of embodiments of the invention enable the creation of a user representation 3000 that is reflective of the user's 2090 natural emotional states, independent of the influence of ingested compounds. This representation provides for personalized therapy, allowing for interventions that are responsive to the user's 2090 current and evolving emotional and cognitive needs.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method for adaptive digital therapy, comprising:
receiving, via an access module comprising at least one of sensors, microphones, cameras, and EEG devices, user data including text, speech, vision, symbols, and brain wave inputs;
processing the received user data through multi-modal deep learning methods executed on a computer processor into processed user data to determine a user's emotional expression, valence, and neuroplastic windows;
mapping the processed user data to a dynamic user representation stored in a non-transitory computer-readable medium;
comparing, using the computer processor, the dynamic user representation to optimal patterns and semantic spaces of a collective stored in a neural library,
deriving a delta from this comparison,
applying generative communications based on the derived delta to adjust the user's current state towards the optimal patterns and semantic spaces; and
transmitting generative communications based on the comparison to the user through the access module, wherein the generative communications are output via at least one of a display, speaker, or haptic feedback device.

2. The method of claim 1, wherein the generative communications include at least one of audio, video, text, photobiomodulation and optogenetic neural modulation, and wherein the method further comprises modifying the generative communications in real-time based on user feedback to adapt a digital therapy.

3. The method of claim 1, wherein the processing of the received user data further comprises:
employing a hierarchical multimodal self-organizing map (HSOM) executed on the computer processor to analyze the text, speech, vision, symbols, and brain wave inputs, wherein the HSOM is configured to represent and process various levels of sensory-motor and symbolic information in a hierarchical structure that mimics neural processing of a human brain;
utilizing a homeostasis management module executed on the computer processor to model the user's physiological and psychological needs and drives based on the analyzed user data, wherein the homeostasis management module suggests personalized behavioral interventions aimed at maintaining the user's emotional and cognitive states within a predetermined homeostatic range;
implementing meta-learning models within the computer processor to optimize a learning process of subordinate machine learning models by adjusting hyperparameters based on the user's interaction with the generative communications, thereby enhancing a cyclical integration of therapeutic experiences over multiple user journeys;
generating the dynamic user representation to include a visual, auditory, or haptic feedback profile that corresponds to the user's preferred mode of receiving the generative communications, wherein the profile is updated in real-time based on the user's engagement with the generative communications; and
outputting the generative communications through an integrated output system comprising the display for visual content, the speaker for auditory content, and the haptic feedback device for tactile content, wherein the integrated output system is controlled by the computer processor to deliver a multi-sensory therapeutic experience that is responsive to the dynamic user representation.

4. A system for providing adaptive digital therapy, comprising:
a hardware access module comprising at least one of sensors, microphones, cameras, and EEG devices, configured to receive user data comprising at least one item selected from the group consisting of text, speech, vision, symbols, and brain wave inputs;
a processor configured to process the received user data using multi-modal deep learning methods to determine a user's emotional expression and valence;
a non-transitory computer-readable medium configured to store a dynamic user representation mapped from the processed user data;
a comparison module comprising a processor and software configured to compare the dynamic user representation to established psychological therapeutic frameworks;
wherein the processor and software of the comparison module are configured to:
execute a hierarchical multimodal self-organizing map (HSOM) to analyze the user data, including the text, the speech, the vision, the symbols, and the brain wave inputs,
represent and process various levels of sensory-motor and symbolic information in a hierarchical structure that mimics neural processing of the human brain, and
organize and interpret the user data to generate the dynamic user representation, and
a communication module comprising wireless interfaces and protocols configured to transmit generative communications to the user based on the comparison.

5. The system of claim 4, wherein the communication module is further configured to modify the generative communications in real-time based on user feedback.

6. The system of claim 4, wherein the processor is further configured to employ adaptive learning algorithms based on developmental robotics principles, the adaptive learning algorithms facilitating a system's evolution by learning from user-generated data reflecting physical interactions and environmental feedback, and wherein the system adapts the digital therapy based on a learned user interaction and environmental feedback patterns, and wherein the processor is further configured to execute a homeostasis management module that models the user's physiological and psychological needs and drives, the module utilizing input data from the user to suggest personalized behavioral interventions aimed at maintaining the user's emotional and cognitive states within a predetermined homeostatic range.

7. The system of claim 4, wherein the processor is further configured to implement meta-learning models that optimize a learning process of subordinate machine learning models within the system by adjusting hyperparameters, thereby enhancing a cyclical integration of therapeutic experiences over multiple user journeys and improving therapeutic outcomes based on a continuous adaptation to the user's evolving emotional and cognitive states.

8. The system of claim 4, wherein the multi-modal deep learning methods include hierarchical multimodal self-organizing maps (HSOMs) configured to represent and process various levels of sensory-motor and symbolic information, thereby organizing and interpreting user data in a hierarchical structure that mimics neural processing of a human brain.

9. The system of claim 4, wherein the processor is further configured to utilize real-time adaptation mechanisms informed by the user's cognitive development, the mechanisms comprising developmental robotics-inspired algorithms that dynamically adjust therapeutic strategies based on a continuous assessment of the user's developmental trajectory and real-time cognitive state, facilitating personalized therapeutic interventions that evolve in synchrony with the user's progress.

10. A method for monitoring a client user's emotional states, comprising:
transmitting user data via an access module, the user data including information about one or more labeled compounds administered to the client user;
transcribing and processing the user data via a computer processor and multi-modal models to determine a user's emotional expression and valence, wherein the processing comprises:
executing a hierarchical multimodal self-organizing map (HSOM) on the computer processor to analyze text, speech, vision, symbols, and brain wave inputs from the user data,
representing and processing various levels of sensory-motor and symbolic information in a hierarchical structure that mimics neural processing of a human brain, and
generating a dynamic user representation based on the analyzed user data;
calculating a valence score quantifying the user's emotional state on a continuum from highly negative to highly positive, wherein the calculating comprises
analyzing physiological data comprising heart rate variability, skin conductance, and brainwave patterns captured by EEG devices,
analyzing linguistic content of the user's speech and text inputs using natural language processing algorithms,
applying a weighted sentiment analysis algorithm that processes the physiological data and linguistic content to calculate a composite valence score,
comparing the composite valence score against predetermined thresholds to categorize the emotional state using a machine learning classifier;
transferring the processed user data and the composite valence score to a data visualization interface for display;
mapping language inputs from the user to a neural library, wherein the mapping comprises:
identifying neural patterns in the user's brain activity that correlate with specific semantic meanings, and
updating the neural library with the identified correlations between the neural patterns and the semantic meanings; and
transmitting generative communications back to the user to create a closed-loop communication system, wherein the generative communications are dynamically adjusted based on the calculated composite valence score and mapped neural patterns to guide the user's emotional state towards an optimal pattern.

11. The method of claim 10, wherein the generative communications are modified based on a metric response indicative of the user's emotional state.

12. The method of claim 10, further comprising dynamically monitoring the user's representation as a lifelog.

13. The method of claim 12, wherein dynamically monitoring the user's representation as a lifelog further comprises:

receiving session data via the access module;
processing the session data within the access module to derive historical patient response metrics indicative of the user's continuous emotional response to various compounds or natural states; and
transferring the patient response metrics from the access module to a remote interface.

14. The method of claim 10, further comprising providing established therapeutic protocols as digital therapy, via:
receiving, at the access module, additional user data during a presentation of generative content;
executing a machine learning model to determine an indication of state associated with the digital therapy based on the additional user data;
determining a modification to the digital therapy based on the indication of state; and
using the indication of state to monitor and adjust the generative content.

15. The method of claim 10, further comprising monitoring the user's dynamic emotional states, via:
transmitting additional user data including information about labeled compounds via the access module;
transcribing and processing the additional user data via multi-modal models to determine the user's updated emotional expression and valence;
calculating and transferring updated processed user data from the access module to the data visualization interface;
updating the neural library based on the additional user data;
mapping embedded meaning and emotional scores of the user's language input to existing therapeutic frameworks; and
transmitting updated generative communications back to the access module to maintain the closed-loop communication system.

16. The method of claim 15, wherein mapping the embedded meaning and emotional scores of the user's language input to existing therapeutic frameworks comprises:
deriving a delta from both collective and individual comparisons within stored data;
logging self-reported flow states to capture heightened metrics that establish baselines for the user;
utilizing long-term memory to identify and record semantic spaces correlated with these metrics to personalize therapeutic interventions to the user based on the derived delta; and
employing adaptive learning algorithms to facilitate system evolution by learning from user-generated data reflecting physical interactions and environmental feedback.

17. The method of claim 15, further comprising:
analyzing the user's real-time emotional and cognitive states using a multi-modal analysis module;
cross-referencing these states with the user's historical data stored in a user profile database;
dynamically generating and delivering personalized therapeutic content that is responsive to the user's unique needs, the content being adapted in real-time to reflect the user's current emotional and cognitive conditions as well as their historical therapeutic responses; and
implementing meta-learning models that optimize a learning process of subordinate machine learning models within the system by adjusting hyperparameters, thereby enhancing cyclical integration of therapeutic experiences over multiple user journeys.

18. A method for training a machine learning model to interpret neural responses as outputs, comprising:
collecting a dataset comprising a wide range of neural responses and corresponding outputs, wherein the neural responses include electrical patterns captured from user brain activity via neural monitoring devices selected from the group consisting of EEG, MEG, or fMRI;
exposing the machine learning model to various neural patterns and words or phrases from the dataset, wherein the exposure involves processing the neural patterns through the model to identify and learn associations between specific brain activities and language elements;
employing supervised learning techniques to train the machine learning model, wherein the trained machine learning model adjusts its parameters based on a comparison of its output to linguistic outputs in the dataset;
validating the trained machine learning model by testing its ability to accurately convert new, unseen neural patterns into linguistic outputs;
integrating the trained machine learning model into a therapeutic system, wherein the trained machine learning model is utilized to interpret real-time neural responses of users into linguistic outputs that facilitate communication or therapeutic feedback; and
continuously updating the trained machine learning model by incorporating new neural responses and linguistic outputs into the dataset, thereby refining the trained machine learning model's accuracy and adaptability over time.

* * * * *